United States Patent
Bise et al.

(10) Patent No.: US 11,398,032 B2
(45) Date of Patent: Jul. 26, 2022

(54) IMAGE ANALYSIS SYSTEM, CULTURE MANAGEMENT SYSTEM, IMAGE ANALYSIS METHOD, CULTURE MANAGEMENT METHOD, CELL GROUP STRUCTURE METHOD, AND PROGRAM

(71) Applicants: Dai Nippon Printing Co., Ltd., Tokyo (JP); TERUMO Kabushiki Kaisha, Tokyo (JP)

(72) Inventors: Ryoma Bise, Tokyo (JP); Yoshitaka Maeda, Tokyo (JP); Masatoshi Kuroda, Tokyo (JP); Kazumasa Yamaki, Tokyo (JP); Ryohei Takeuchi, Kanagawa (JP); Fumiya Ohashi, Kanagawa (JP); Kouichirou Yori, Kanagawa (JP)

(73) Assignees: DAI NIPPON PRINTING CO., LTD., Tokyo (JP); TERUMO KABUSHIKI KAISHA, Tokyo (JP)

( * ) Notice: Subject to any disclaimer, the term of this patent is extended or adjusted under 35 U.S.C. 154(b) by 865 days.

(21) Appl. No.: 16/317,741

(22) PCT Filed: Jul. 13, 2017

(86) PCT No.: PCT/JP2017/025596
§ 371 (c)(1),
(2) Date: Jan. 14, 2019

(87) PCT Pub. No.: WO2018/012601
PCT Pub. Date: Jan. 18, 2018

(65) Prior Publication Data
US 2019/0236784 A1 Aug. 1, 2019

(30) Foreign Application Priority Data
Jul. 14, 2016 (JP) .............................. JP2016-139325

(51) Int. Cl.
*G06T 7/00* (2017.01)
*G06T 7/20* (2017.01)
(Continued)

(52) U.S. Cl.
CPC ............. *G06T 7/0016* (2013.01); *C12M 1/00* (2013.01); *C12M 41/00* (2013.01); *C12M 41/36* (2013.01);
(Continued)

(58) Field of Classification Search
CPC ....... G06T 7/0016; G06T 7/0012; G06T 7/20; G06T 2207/10016; G06T 2207/10056;
(Continued)

(56) References Cited

U.S. PATENT DOCUMENTS 10,416,433 B2 * 9/2019 Matsumoto ............ G06V 10/44
10,591,402 B2 * 3/2020 Ikuyama .................. C12M 1/34
(Continued)

FOREIGN PATENT DOCUMENTS

JP 2009-229276 10/2009
JP 2011-229410 11/2011
(Continued)

OTHER PUBLICATIONS

Bahnson, et al. "Automated measurement of cell motility and proliferation" BMC Cell Biology, vol. 6, No. 1, Apr. 14, 2005, p. 19.
(Continued)

*Primary Examiner* — Shefali D Goradia
(74) *Attorney, Agent, or Firm* — Hamre, Schumann, Mueller & Larson, P.C.

(57) ABSTRACT

[Problem] To evaluate objective cell groups by estimating a mixing ratio of objective cell group without affecting treatment itself and its production process when the objective cell groups include plural kinds of cell groups having different attributes, and to provide an image analysis system
(Continued)

and a culture management system capable of accurately perform a quality control and a production control with low cost.

[Solution] The cell quality evaluation system 1 detects a feature amount in each cell easily analyzable from images, and estimates a mixing ratio of each of plural kinds of cell groups included in the objective cell groups based on a distribution of the detected feature amount and pre-recorded information of the feature amount. As the feature amount, the embodiment uses a migration speed of each cell, easily distinguishable by analyzing tracking of each cell from plural images in time series.

17 Claims, 12 Drawing Sheets

(51) Int. Cl.
C12M 1/34 (2006.01)
C12M 1/00 (2006.01)
G06V 10/50 (2022.01)
G06V 20/69 (2022.01)

(52) U.S. Cl.
CPC .............. *G06T 7/0012* (2013.01); *G06T 7/20* (2013.01); *G06V 10/50* (2022.01); *G06V 20/69* (2022.01); *G06V 20/693* (2022.01); *G06V 20/698* (2022.01); *G06T 2207/10016* (2013.01); *G06T 2207/10056* (2013.01); *G06T 2207/20072* (2013.01); *G06T 2207/30024* (2013.01)

(58) Field of Classification Search
CPC ........... G06T 2207/20072; G06T 2207/30024; G06V 20/698; G06V 20/693; G06V 20/69; G06V 10/50; C12M 1/00; C12M 41/00; C12M 41/36
See application file for complete search history.

(56) References Cited

U.S. PATENT DOCUMENTS

| 2009/0130703 | A1 | 5/2009 | Wagner et al. |
| 2011/0019897 | A1* | 1/2011 | Takagi ............ G06V 20/695 382/133 |
| 2011/0165143 | A1* | 7/2011 | Li .................. A61K 38/06 514/19.3 |
| 2012/0134571 | A1* | 5/2012 | Ito ................. C12M 41/46 382/133 |
| 2013/0078647 | A1 | 3/2013 | Wagner et al. |
| 2014/0248648 | A1 | 9/2014 | Chirila et al. |
| 2016/0232682 | A1 | 8/2016 | Nakagawa et al. |
| 2017/0061618 | A1 | 3/2017 | Matsubara |

FOREIGN PATENT DOCUMENTS

| JP | 2011229409 A * | 11/2011 | ............ C12M 41/14 |
| JP | 2012-511909 | 5/2012 | |
| JP | 2014-526031 | 10/2014 | |
| JP | 2015-001859 | 1/2015 | |
| JP | 2017-023055 | 2/2017 | |
| WO | 2015/041177 | 3/2015 | |
| WO | 2015/182396 | 12/2015 | |

OTHER PUBLICATIONS

Extended European Search Report issued in European Patent Application No. 17827724.0, dated May 29, 2019, 6 pages.

Yin, et al., "Understanding the Phase Contrast Optics to Restore Artifact-Free Microscopy Images for Segmentation" Medical Image Analysis 16, (5): 1047-1062(2012).

Yin, et al., "Cell Segmentation in Microscopy Imagery Using a Bag of Local Bayesian Classifiers" IEEE International Symposium on Biomedical Imaging (ISBI) 2010,4 pages.

Bise, et al., "Reliable Cell Tracking By Global Data Association" IEEE International Symposium on Biomedical Imaging 2011, p. 1004-1010.

Kanade, et al., "Cell Image Analysis: Algorithms, System and Applications" IEEE Workshop on Applications of Computer Vision (WACV) 2011, 8 pages.

* cited by examiner

MIXED DISTRIBUTION FUNCTION

DISTRIBUTION FUNCTION ($N_1$)

DISTRIBUTION FUNCTION ($N_2$)

MIXED DISTRIBUTION FUNCTION (LOG)

DISTRIBUTION FUNCTION (LOG ln{$N_1$})

DISTRIBUTION FUNCTION (LOG ln{$N_2$})

IMAGE ANALYSIS SYSTEM, CULTURE MANAGEMENT SYSTEM, IMAGE ANALYSIS METHOD, CULTURE MANAGEMENT METHOD, CELL GROUP STRUCTURE METHOD, AND PROGRAM

TECHNICAL FIELD

This disclosure relates to an image analysis system which analyzes objects of culture such as cells and germs using images, and also relates to a culture system and a culture management system using the image analysis system.

BACKGROUND TECHNIQUE

Recently, according to progress in medical technology such as regenerative medicine and infertility treatment, there is an advance in technology of observing and evaluating situations of proliferation or inhibition of cells non-invasively and easily for objective cells (hereinafter referred to as "objective cells") and objective cell groups (hereinafter referred to as "objective cell groups").

Particularly, as a non-invasive method, there is recently known a technique of imaging objective cells and objective cell groups and analyzing the images to observe cells of interest. For example, there are known a technique of detecting each cell using time-lapse images in time series (e.g., Non-Patent References 1 and 2) and a tracking technique of tracking each cell (e.g., Non-Patent References 3 and 4).

Also, there are known an imaging device quantitatively grasping moving states of cells of interest using a plurality of images (e.g., Patent Reference 1), and a device calculating feature amounts indicating different forms of cells from a plurality of images and evaluating each cell based on the feature amounts (e.g., Patent Reference 2).

PRIOR ART REFERENCES

Patent References

Patent Reference 1: Japanese Patent Application laid-Open under No. 2009-229276
Patent Reference 2: Japanese Patent Application laid-Open under No. 2011-229410
Non-Patent Reference 1: Zhaozheng Yin, Takeo Kanade, Mei Chen: "Understanding the Phase Contrast Optics to Restore Artifact-Free Microscopy Images for Segmentation", Medical Image Analysis 16(5): 1047-1062 (2012)
Non-Patent Reference 2: Zhaozheng Yin, Ryoma Bise, Mei Chen and Takeo Kanade: "Cell Segmentation in Microscopy Imagery Using a Bag of Local Bayesian Classifiers", IEEE International Symposium on Biomedical Imaging (ISBI) 2010
Non-Patent Reference 3: Ryoma Bise, Zhaozheng Yin, Takeo Kanade: "Reliable Cell Tracking By Global Data Association", IEEE International Symposium on Biomedical Imaging 2011
Non-Patent Reference 4: Takeo Kanade, Zhaozheng Yin, Ryoma Bise, Seungil Huh, Sungeun Eom, Michael Sandbothe and Mei Chen: "Cell Image Analysis: Algorithms, System and Applications", IEEE Workshop on Applications of Computer Vision (WACV) 2011

SUMMARY OF THE INVENTION

Problem to be Solved by the Invention

However, not only recognizing a number of objective cells, but also confirming mixture of other cell species different from cell species of the objective cells is required because it affects treatment itself and its production process. In the devices of the above-mentioned Patent References, when cell groups subjected to evaluation and observation include plural kinds of cell groups having different attributes, it is difficult to easily estimate the number of the cell groups and a ratio of each cell group with keeping non-invasiveness.

The present invention is made to solve the above problem. Its object is to non-invasively estimate a mixing ratio of the cell group without affecting the treatment itself and its production process when the objective cell groups include plural kinds of cell groups having different attributes, and consequently to provide an image analysis system and a culture management system using the image analysis system, which are capable of accurately performing evaluation and a quality control of the objective cell groups and its production control with low cost.

Means for Solving the Problem

In order to solve the above problem, an image analysis system of this disclosure includes:
an acquisition unit configured to acquire data of plural objective images, in which objective cell groups including plural kinds of cell groups having different attributes are imaged, in time series;
a detection unit configured to detect a migration speed of each cell imaged in the objective images by analyzing the acquired plural objective images;
a generation unit configured to generate a distribution function or a distribution state of the migration speeds of the imaged objective cell groups based on the detected migration speed of each cell; and
an estimation unit configured to estimate a mixing ratio of each of the plural kinds of cell groups based on migration speed information, recorded in a storage unit in advance and including information of the migration speed of each of the plural kinds of cell groups, and the generated distribution function or the generated distribution state.

With this configuration, the image analysis system of this disclosure can estimate mixing ratios of the objective cell groups including plural kinds of cell groups having different attributes (e.g., attributes distinguished by characteristic or function such as doubling time) by analyzing images, and hence can estimate the mixing ratios of the objective cell groups non-invasively and accurately.

Accordingly, the image analysis system of this disclosure can estimate a ratio of a specific cell species (e.g., skeletal myoblast) by using the images when cell groups other than the specific cell group to be used are mixed in the objective cell groups. Thus, it is possible to evaluate quality of the objective cell groups, e.g., calculation of purity of the specific cell species included in the objective cell groups, and it is also possible to evaluate a culture state of the objective cell groups during or after the culture, e.g., cell death of the specific cell species or mutation to other cell species during culture.

As a result, the image analysis system of this disclosure can perform not only quality control of the objective cell groups and the specific cell species, but also production control of the cell species easily and accurately.

Also, in order to solve the above problem, this disclosure includes a culture management system which manages a state of objective cell groups including plural kinds of cell groups having different attributes in a predetermined culture period, comprising:

an acquisition unit configured to acquire data of plural objective images, in which objective cell groups including plural kinds of cell groups having different attributes are imaged, in time series at a predetermined timing in the culture period;

a detection unit configured to detect a migration speed of each cell imaged in the objective images by analyzing the acquired plural objective images;

a generation unit configured to generate a distribution function or a distribution state of the migration speeds of the imaged objective cell groups based on the detected migration speed of each cell;

an estimation unit configured to estimate a mixing ratio of each of the plural kinds of cell groups based on migration speed information, recorded in a storage unit in advance and including information of the migration speed of each of the plural kinds of cell groups, and the generated distribution function or the generated distribution state;

a determination unit configured to execute determination processing which determines whether or not the mixing ratio of each of the plural kinds of cell groups at the predetermined timing satisfies a predetermined mixing ratio condition; and a notification unit configured to execute a predetermined notification of a result of the determination processing to a manager.

With this configuration, the culture management system of this disclosure can manage the culture of the objective cell groups having plural kinds of cell groups having different attributes, so as to prevent that cell species other than the specific cell species to be used increases in the objective cell groups more than a prescribed degree during the culture period and the cell species in the objective cell groups becomes unusable for regenerative medicine, for example.

Particularly, in case of the objective cell groups including cell groups of plural kinds of cell species having different doubling times, such as the objective cell groups collected from a living body (specifically muscle fibers) formed by the skeletal myoblasts and the fibroblasts, the culture management system can continue the culture of the cell groups of necessary cell species such as the skeletal myoblasts, while preventing the culture of the cell groups of unnecessary cell species such as the fibroblasts. Therefore, it becomes possible to culture useful objective cell groups including necessary cell species with a high mixing ratio.

Accordingly, the culture management system of this disclosure can perform quality control of the objective cell groups during the culture, and make the manager to control the culture of the objective cell groups while performing the quality control, thereby improving production efficiency of the objective cell groups.

Also, in order to solve the above problem, this disclosure includes a cell production method for producing at least a specific kind of cell group by controlling culture of objective cell groups collected from a living body and including plural kinds of cell groups having different attributes in a predetermined culture period, the method comprising the steps of:

executing inspection processing including determination processing which determines whether or not a mixing ratio of each of the plural kinds of cell groups included in the objective cell groups being cultured at a predetermined timing in the culture period satisfies a predetermined mixing ratio condition; and executing inhibition processing of inhibiting culture of unnecessary cell species in the objective cell groups when the mixing ratio of each of the plural kinds of cell groups does not satisfy the mixing ratio condition, or executing preparation processing for executing the inhibition processing, wherein the inspection processing comprising the steps of:

acquiring data of plural objective images, in which the objective cell groups including plural kinds of cell groups having different attributes are imaged, in time series at a predetermined timing;

detecting a migration speed of each cell imaged in the objective images by analyzing the acquired plural objective images;

generating a distribution function or a distribution state of the migration speeds of the imaged objective cell groups based on the detected migration speed of each cell; and estimating a mixing ratio of each of the plural kinds of cell groups based on migration speed information, recorded in a storage unit in advance and including information of the migration speed of each of the plural kinds of cell groups, and the generated distribution function or the generated distribution state, and executing the determination processing based on the mixing ratio condition.

With this configuration, when the mixing ratio of the cell species other than the specific cell species, used for regenerative medicine for example, increases more than a specified degree, the cell group production method of this disclosure can inhibit the culture of cell groups of such cell species, thereby to surely culture the objective cell groups usable in the regenerative medicine.

Accordingly, the cell group production method of this disclosure can culture and produce the objective cell groups of proper quality, thereby improving production efficiency of the objective cell groups.

Effect of the Invention

This disclosure enables to estimate the mixing ratios of the objective cell groups non-invasively and accurately. Therefore, it is possible to perform quality control of the objective cell groups and the specific cell species as well as production control of the cell species easily and accurately.

DESCRIPTION OF EMBODIMENTS TO EXERCISE INVENTION

Preferred embodiments of the present invention will be described below with reference to the attached drawings. The following embodiments are directed to a case where an image analysis system, a culture management system, an image analysis method, a culture management method, a cell production method and a program according to the present invention are applied to a cell quality evaluation system performing quality control of objective cell groups using images of the objective cell groups created by imaging cultured cell groups and a culture management system using the cell quality control system. However, the present invention is not limited to the following embodiments within the range including its technical idea.

[A] 1st Embodiment

[A1] Outline of a Cell Quality Evaluation System

Figure 1:
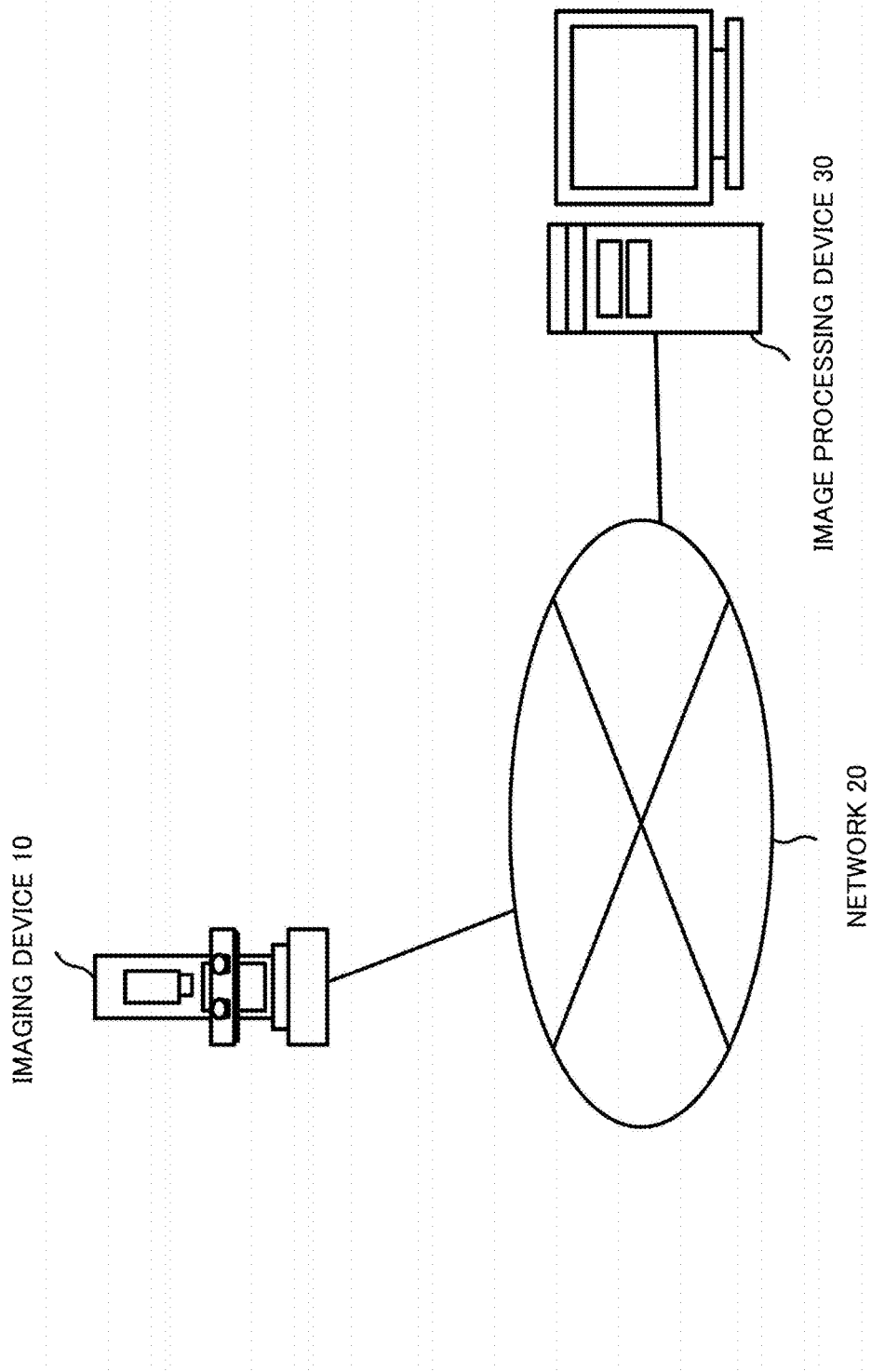
FIG. 1 is a diagram illustrating a configuration of a cell quality evaluation system according to a first embodiment of the present invention.

First, a configuration and an outline of a cell quality evaluation system according to the first embodiment will be described with reference to FIG. 1. FIG. 1 is a system configuration diagram illustrating a configuration of the cell quality evaluation system 1 according to this embodiment.

The cell quality evaluation system 1 according to this embodiment images objective cell groups placed in a specific container such as a dish and including plural kinds of cell groups having different attributes, and executes image analysis of the imaged objective cell groups (hereinafter referred to as "an objective image"). Thus, the cell quality evaluation system 1 estimates a mixing ratio of the plural kinds of cell groups, and evaluates the quality of the objective cell groups based on the estimated mixing ratio.

For example, when skeletal myoblasts collected from a living body of a person (donor) are subcultured, it is important to confirm a state (a culture state) of the skeletal myoblasts after culture, e.g., whether or not the number of the skeletal myoblasts after culture reaches a sufficient number for use in treatment, or whether or not the skeletal myoblasts of good quality are cultured (normally differentiated).

Particularly, even if cells collected from a living body (e.g., a human body) are cleaned and the cleaned cells are separated and recovered, not a few fibroblasts remain in the cell groups, and it is difficult to completely remove the fibroblasts to culture only the skeletal myoblasts as the objective cell.

Therefore, when the objective cells are cultured in such a state, the ratio of the skeletal myoblasts in the objective cell groups after culture becomes unknown. The skeletal myoblast has such a characteristic that its proliferation rate is slower than the fibroblast, and the number of the cells of the skeletal myoblast and the ratio of the skeletal myoblasts to whole cells cannot be specified until the culture ends.

Also, during subculture of the skeletal myoblasts, the same skeletal myoblast sometimes changes to a cell having a different attribute due to cell deaths, mutation of form, or maturity. In such a case, it is extremely important to recognize the ratio of appropriate skeletal myoblasts and inappropriate skeletal myoblasts for use in treatment or experiments.

On the other hand, by an invasive method such as a method using reagent, it is possible to estimate the mixing ratio of the plural kinds of cell groups to the objective cell groups and its quality. However, in this case, reagent affects the human body, and it becomes difficult to use the cells such as the skeletal myoblasts in treatment.

On the contrary, in a field of cell culture, even in cell groups having different attributes, the characteristic of each cell (i.e., specific predetermined feature amount) may be the same or may belong to the same range according to individual differences and a situation of culture environment.

Particularly, a speed at the time of cell migration known as a feature amount used for analyzing characteristic of each cell, i.e., a migration speed, can be easily obtained by tracking movement of each cell in the plural time-series images. However, the migration speed is not uniquely determined for each cell species having different attributes due to the state of the donor such as health at the time of collection, the culture environment or the culture state, or property of each cell, and is distributed in a certain range.

Therefore, in this embodiment, the migration speed is detected as a feature amount in each cell, which is easily analyzable from images, and the mixing ratio of each of the plural kinds of cell groups included in the objective cell groups is estimated based on the distribution of the detected migration speed and a pre-recorded migration speed information.

Specifically, the cell quality evaluation system 1 according to this embodiment includes an imaging device 10 which images the objective cell groups in time series to generate image data (hereinafter referred to as "objective image data"), a network 20, and an image processing device 30 which estimates the mixing ratio of the objective cell groups imaged into the objective image data and evaluates the quality of the objective cell groups.

The imaging device 10 includes, for example, a communication function of connecting to the network 20 to transmit and receive data, an imaging function of acquiring prescribed images such as time-lapse images, and a microscope function of observing the cells.

Particularly, by the imaging function, the imaging device 10 takes still pictures of the objective cell groups placed on the dish at every fixed interval (e.g., 6 minutes or 12 minutes) to generate the objective image data as the time-lapse images, and transmits the generated objective image data to the image processing device 30 together with time information indicating an imaging time.

For example, the imaging device 10 includes an optical system, a CCDI sensor (Charge Coupled Device Image sensor) which converts optical images inputted from the optical system to an electric signal, and a generating unit which generates the image data based on the electric signal generated by the CCDI sensor.

Also, the imaging device 10 transmits the objective image data to the image processing device 30 directly by wired transmission or by wireless transmission via an access point not shown, using a predetermined communication standard such as LAN (Local Area Network).

For example, the network 20 may be a wired or wireless IP (Internet Protocol) network, or may be a network of a public telephone line including a portable telephone network.

In cooperation with the imaging device 10, the image processing device 30 analyses the objective image data generated by the imaging device 10 to estimate the mixing ratios of plural kinds of cell groups, and evaluates the quality of the objective cell groups based on the estimated mixing ratios.

Specifically, the image processing device 30 executes processing of (hereinafter referred to as "quality determination processing):

(1) acquiring plural objective images of the objective cell groups from the imaging device 10 in time series, (2) detecting a migration speed of each cell in the objective images by performing image analysis of the acquired plural objective images, (3) generating a distribution function or a distribution state of the migration speeds of the imaged objective cell groups based on the detected migration speed of each cell, (4) estimating a mixing ratio of each of the plural kinds of cell groups based on the pre-recorded migration speed information indicating migration speeds of each of the plural kinds of cell groups and the generated distribution function or the generated distribution state, and (5) determining the quality of the objective cell groups as passed when the estimated mixing ratio satisfies a predetermined condition.

Particularly, in this embodiment, the image processing device 30 uses a normal distribution or a log normal distribution as the distribution function, based on the detected migration speed of each cell.

With the above configuration, the cell quality evaluation system 1 of this embodiment can estimate the mixing ratios of the objective cell groups non-invasively and accurately. Therefore, the cell quality evaluation system 1 can evaluate the quality of the objective cell groups such as calculation of a purity of certain cell species contained in the objective cell groups, and evaluate the culture state of the objective cell groups during or after the culture, such as cell deaths of a certain cell species or mutation to other cell species during culture.

Therefore, the cell quality evaluation system 1 of this embodiment can perform not only the quality control of the objective cell groups and certain objective cell species but also the production control of the cell species easily and accurately.

It is noted that the following description is directed to the case where the image processing device 30 estimates the mixing ratios of the plural kinds of cell groups based on the distribution function of the migration speed of the imaged objective cell groups and the pre-recorded migration speed information.

Also, while the following description uses the skeletal myoblasts and the fibroblasts at the skeletal muscle as the cell groups included in the objective cell groups, this embodiment may be applied to stem cells, the cell groups obtained by differentiation-inducing the stem cells, or target cells and other cells collected together with the target cells at the time of collecting from a body of a patient, for example:

(1) cell groups of corneal epithelial cells, corneal parenchymal cells and corneal endothelial cells at the cornea, (2) cell groups of myocardial cells, vascular endothelial cells and fibroblasts at the cardiac muscle, (3) cell groups of epidermal keratinocyte and fibroblasts at the skin, (4) cell groups of retinal pigment epithelial cells, fibroblasts and vascular endothelial cells at the retina, and (5) cell groups of mucosal epithelial cells, epidermal keratinocyte and fibroblasts at the mucous membrane.

Further, in this embodiment, the expression "different attributes" not only means the difference in the functions and the cell species like the skeletal myoblasts and the fibroblasts, but also means the difference in maturities indicating that the state of differentiation and undifferentiation or the intercellular adhesion advance to become a transplantable state, the difference in the external shapes such as shapes and sizes or structures, and the difference in presence/absence of mutation, injection of predetermined factor or fusion with other cell during culture.

[A2] Image Processing Device

Figure 2:
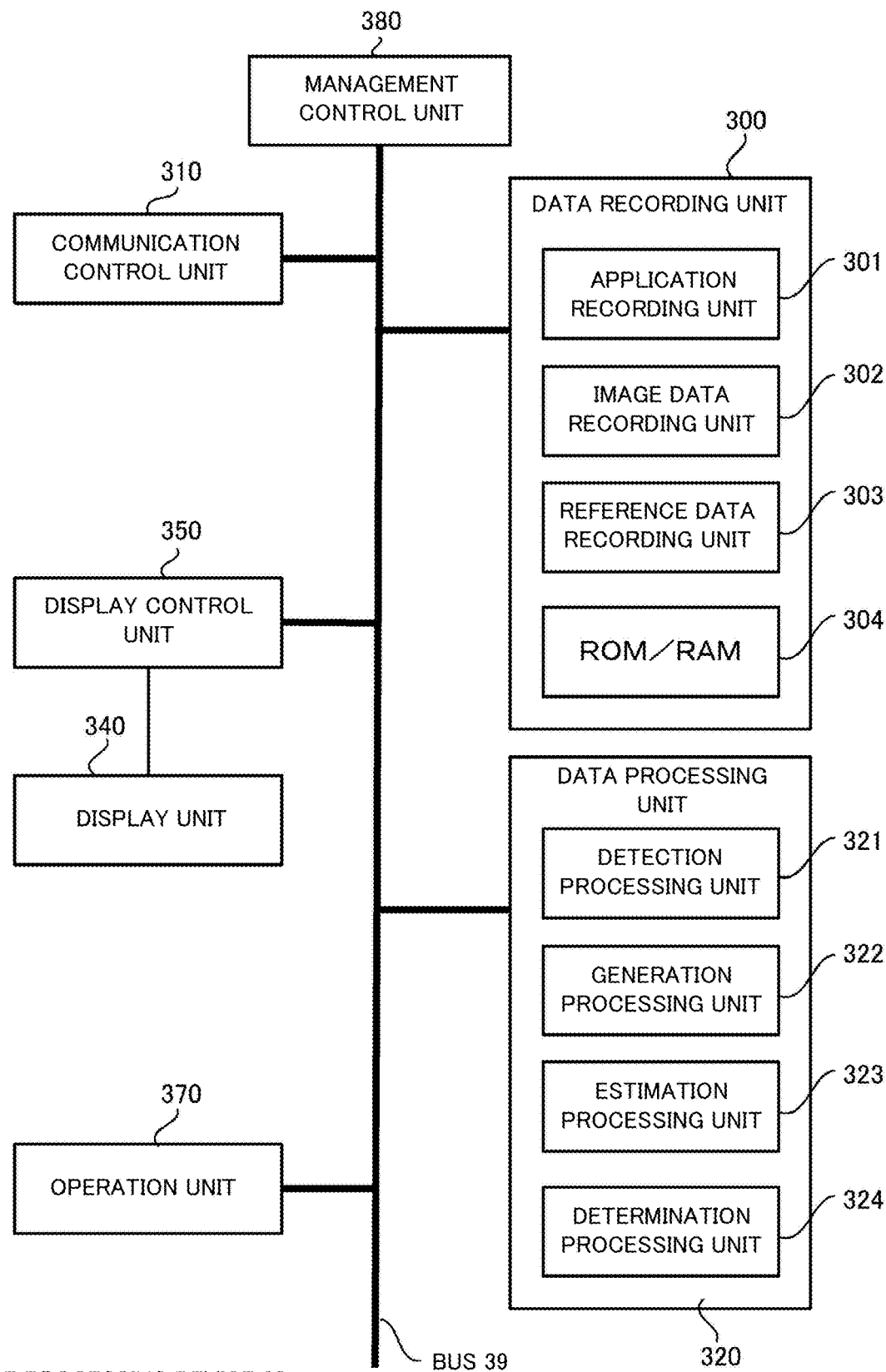
FIG. 2 is a block diagram illustrating a configuration of an image processing device of the cell quality evaluation system according to the first embodiment.

Next, a configuration of the image processing device 30 of this embodiment will be described with reference to FIG. 2. FIG. 2 is a block diagram illustrating blocks of the image processing device 30 of this embodiment.

Specifically, as shown in FIG. 2, the image processing device 30 of this embodiment includes a data recording unit 300 which records various data used when various programs are executed, a communication control unit 310 which transmits and receives various data such as time-series data of the objective cell groups transmitted from the imaging device 10, a data processing unit 320 which executes quality determination processing based on the generated objective images, a display unit 340 including a liquid-crystal display, a display control unit 350 which controls the display unit 340, an operation unit 370, and a management control unit 380 which controls each block. The above blocks are connected with each other via a bus 39 to enable data transmission between each block.

The data recording unit 300 may be a HDD (Hard Disk Drive) for example, and includes an application recording unit 301 which records application programs for executing each processing such as quality determination processing, an image data recording unit 302 which records image data imaged and generated by the imaging device 10, a reference data recording unit 303 which records various data such as migration speed information and thresholds used in the quality control processing, and a ROM/RAM 304 used as a work area during execution of each program.

Particularly, the image data recording unit 302 records objective image data acquired from the imaging device 10 and generated by imaging plural objective cell groups in time series for each dish (i.e., for each group).

The reference data recording unit 303 records the migration speed information of the cell groups included in the objective cell groups to be estimated. For example, in this embodiment, the reference data recording unit 303 records the values of an average speed and a variance (standard deviation) of the skeletal myoblast and the fibroblast as the migration speed information.

The communication control unit 310 is a certain network interface, and establishes a communication line with the imaging device 10 to transmit and receive various data acquired by the imaging device 10.

The data processing unit 320 executes the following processing based on the applications for executing the quality determination processing recorded in the ROM/RAM 304:

(1) processing of detecting the migration speed of each cell imaged in the objective images by executing image analysis of the plural objective images acquired from the imaging unit 10 in a time-series manner (hereinafter referred to as "migration speed detection processing"), (2) processing of generating the distribution function related to the migration speed of the imaged objective cell groups based on the detected migration speed of each cell (hereinafter referred to as "distribution function generation processing"), (3) processing of estimating the mixing ratio of each of the plural kinds of cell groups based on the pre-recorded migration speed information and the generated distribution function (hereinafter referred to as "mixing ratio estimation processing"), and (4) processing of determining the quality of the objective cell groups as passed when the estimated mixing ratio satisfies the predetermined condition (hereinafter referred to as "pass determination processing").

Particularly, by executing the applications, the data processing unit 320 realizes a detection processing unit 321 which executes the migration speed detection processing, a generation processing unit 322 which executes the distribution function generation processing, an estimation processing unit 323 which executes the mixing ratio estimation processing and a determination unit 324 which executes the pass determination processing.

For example, the detection processing unit 321 of this embodiment constitutes the acquiring unit of the present invention together with the communication control unit 310, and constitutes the detection unit of the present invention. Also, for example, the generation processing unit 322 of this embodiment constitutes the generation unit of the present invention, and the estimation processing unit 323 constitutes the estimation unit of the present invention. Further, for example, the determination processing unit 324 of this embodiment constitutes the determination unit of the present invention.

The detail of each block in the data processing unit 320 of this embodiment will be described later.

The display unit 340 includes a panel of liquid-crystal elements or EL (Electro Luminescence) elements, and displays certain images based on the display data generated by the display control unit 350.

Under the control of the management control unit 380 and the data processing unit 320, the display control unit 350 generates drawing data necessary to make the display unit 340 draw certain images, and outputs the generated drawing data to the display unit 340.

The operation unit 370 includes various kinds of confirmation buttons, operation buttons for inputting operation commands and numeric keypads formed by a touch sensor provided on the display unit 340, and is used for each operation.

The management control unit 380 mainly includes a central processing unit (CPU), and performs total management control of the image processing unit 30 and other various controls by executing the programs.

The ROM/RAM 304 records various programs necessary for the operation of the image processing device 30. Also, the ROM/RAM 304 records various applications to be executed by the data processing unit 320 and the management control unit 380. The ROM/RAM 340 is used as a work area during execution of each program.

[A3] Data Processing Unit

Figure 3A:
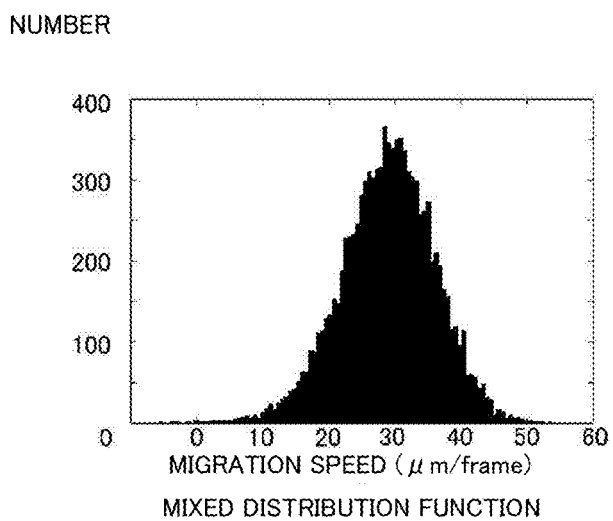
FIG. 3A is a diagram for explaining mixing ratio estimation processing (mixed distribution function) executed by the image processing device according to the first embodiment.
Figure 3B:
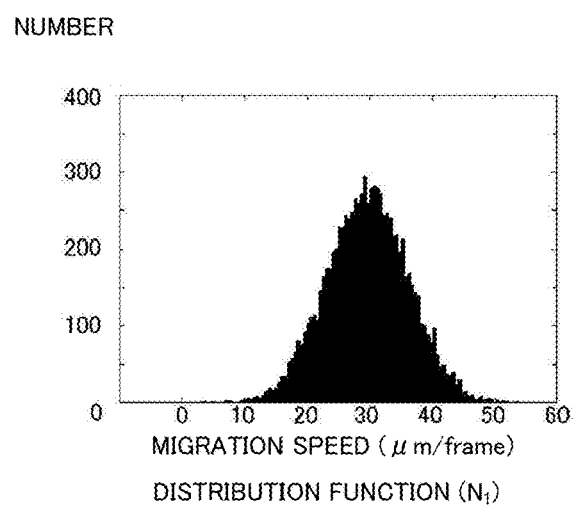
FIG. 3B is a diagram for explaining mixing ratio estimation processing (distribution function $N_1$) executed by the image processing device according to the first embodiment.
Figure 3C:
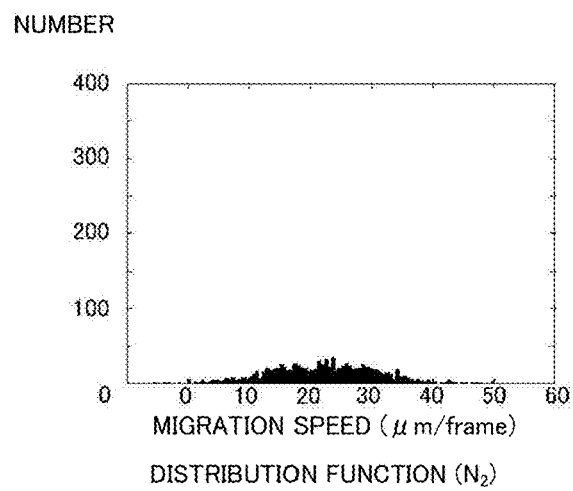
FIG. 3C is a diagram for explaining mixing ratio estimation processing (distribution function $N_2$) executed by the image processing device according to the first embodiment.

Next, the detail of the data processing unit 320 in the image processing device 30 of this embodiment will be described with reference to FIGS. 3A to 3C. FIGS. 3A to 3C are diagrams for explaining the mixing rate estimation processing (the mixed distribution function, the distribution function $N_1$ or the distribution function $N_2$) executed by the estimation processing unit 323 of this embodiment.

For example, while using the technique described in the above-mentioned Non-Patent References 1 to 4, the detection processing unit 321 acquires a plurality of time-series objective images (the time-lapse images) of the objective cell groups placed on the dish and imaged by the imaging device 10 from the image data recording unit 302, identifies tracking of each cell included in each objective image by analyzing each of the acquired objective images, and executes the migration speed detection processing which detects the migration speed of each cell.

Specifically, the detection processing unit 321 detects an area having high luminance and surrounded by Halo, which is a bleeding of light appearing at the circumference of the image, as a cell by using the time-lapse images (phase contrast images) for each of a predetermined time interval and plural time-series time-lapse images, and detects cell divisions based on the variation of the cell shape using a probability model such as EDCRF.

Particularly, the detection processing unit 321 recognizes partially-overlapped cell shapes based on the cells detected in the immediately preceding frame to specify a moved position (coordinates (x,y) in the objective image) of the same cell, and then calculates a movement distance of each cell based on the coordinates in the previous and following objective images in time series.

Then, the detection processing unit 321 detects the migration speed of each cell based on the calculated movement distance and the time difference of the objective images, and stores the detected migration speed of each cell in the ROM/RAM 304.

In this embodiment, it is sufficient to detect the migration speeds of the cells of about 1000 samples. For example, when the objective cell groups include 100 cells (or it is supposed that the objective cell groups include 100 cells), the detection processing unit 321 may execute the migration speed detection processing based on the objective images (time-lapse images) of about 10 frames.

Also, the detection processing unit 321 may identify each cell in each objective image by a manual operation of a worker using the operation unit 370, and may compare the plural times-series objective images to identify the moved position of the same cell.

The generation processing unit 322 executes the distribution function generation processing which calculates the distribution function of the normal distribution or the log normal distribution of the detected migration speed of each cell.

Specifically, supposing that the migration speed of each cell becomes the normal distribution or the log normal distribution, the generation processing unit 322 calculates an average value and a variance value of the migration speed of each cell, and calculates the distribution function of the normal distribution or the log normal distribution using the average values and the variance values thus calculated.

For example, the generation processing unit 322 calculates the average value "$\mu$" and the variance value "$\sigma$" in case of supposing the normal distribution of the migration speed of each cell, or calculates the average value "$\mu_x$" and the variance value "$\sigma_x$" in the log normal distribution, and calculates the normal distribution function $N_1(x)$ expressed by the equation (1) or the log normal distribution function $N_2(x)$ expressed by the equation (2) as the mixed distribution function.

$$N_1(x) = N_1(X \mid \mu, \sigma) = \frac{1}{\sqrt{2\pi\sigma^2}} \exp\left(-\frac{(x-\mu)^2}{2\sigma^2}\right) \quad (1)$$

$$N_2(x) = N_2(X \mid \mu_x, \sigma_x) = \frac{1}{\sqrt{2\pi\sigma_x^2}} \exp\left(-\frac{(\ln(x)-\mu_x)^2}{2\sigma_x^2}\right) \quad (2)$$

The estimation processing unit 323 executes the mixing ratio estimation processing for calculating the mixing ratio of the cell group based on the normal distribution function or the log normal distribution function thus calculated (i.e., the mixed distribution function) and the migration speed information of the cell groups included in the objective cell groups to be estimated and pre-recorded in the reference data recording unit 303.

Normally, since the migration speed of each cell group is independent (not dependent) from the migration speed of other cell group, it is supposed that the migration speed of each cell is in accordance with the distribution of the migration speed of each cell group, specifically the normal distribution or the log normal distribution. In the observed mixed distribution (specifically, the average and the variance) of each cell group, if a basic distribution (specifically, the average and the variance) of each cell group included in the objective cell groups is known, the mixing ratio can be estimated by statistical processing using a predetermined algorithm.

Therefore, the estimation processing unit 323 estimates the mixing ratio of each of the plural kinds of cell groups based on the average speed and the variation (the standard deviation) serving as the migration speed information of each cell group included in the objective cell groups to be estimated, and the normal distribution function $N_1(x)$ of the equation (1) or the log normal distribution function $N_2(x)$ of the equation (2) calculated by the generation processing unit 322.

Specifically, in the case where the mixing ratio is calculated for two cell groups, i.e., the cell group A (e.g., the skeletal myoblast) and the cell group B (e.g., the fibroblast) and the normal distribution function (i.e., the function indicating the mixed distribution) calculated by the generation processing unit 322 is the mixed distribution function f(x) shown in FIG. 3A, the estimation processing unit 323 calculates the variables of the mixing ratio "$\pi_A$" and "$\pi_B$" satisfying the equations (3) and (4) based on a predetermined algorithm, and determines the ratio of the distribution functions shown in FIGS. 3B and 3C. It is noted that the equation (3) is an equation of the mixed distribution function f(x) in case of the normal distribution function.

$$f(x) = \pi_A N_1(x_A) + \pi_B N_2(x_B) \quad (3)$$
$$= \pi_A \frac{1}{\sqrt{2\pi\sigma_A^2}} \exp\left(-\frac{(x-\mu_A)^2}{2\sigma_A^2}\right) + \pi_B \frac{1}{\sqrt{2\pi\sigma_B^2}} \exp\left(-\frac{(x-\mu_B)^2}{2\sigma_B^2}\right)$$

$$\pi_A + \pi_B = 1 \quad (4)$$

In this embodiment, the average values "$\mu_A$" and "$\mu_B$" and the variance values "$\sigma_A$" and "$\sigma_B$" in the equation (3) are known from the migration speed information. For example, when the normal distribution function $N_1(x_A)$ is skeletal myoblast, "$\mu_A$" is 29.72857 μm/frame and "$\sigma_A$" is 6.602264. When the normal distribution function $N_2(x_B)$ is fibroblast, "$\mu_B$" is 22.5 μm/frame and "$\sigma_B$" is 8.921323.

In this embodiment, as the predetermined algorithm, the estimation processing unit 323 uses EM (Expectation Maximization) algorithm which is one of maximum likelihood methods. Specifically, the estimation processing unit 323 calculates the parameter variables "$\pi_A$" and "$\pi_B$" at which the log likelihood function ln(p) of the equation (5) becomes maximum.

$$\ln p(X|\mu,\sigma,\pi) = \Sigma_{m=1}^{M} \ln\{\Sigma_{k=1}^{K} \pi_k N(x_n|\mu,\sigma)\} \quad (5)$$

Particularly, in the equation (5), the estimation processing unit 323 first calculates an initialized value of the variable "$\pi_k$" using the average value "$\mu$" and the variance value "$\sigma$". Then, the estimation processing unit 323 calculates a burden rate "$\gamma(z_{nk})$" at the k-th variable with respect to the n-th factor (i.e., corresponding normal distribution function N(x)), calculates next variable "$\pi_k^{new}$", and calculates the parameter variables "$\pi_A$" and "$\pi_B$" at which the log likelihood function ln(p) of the equation (5) becomes maximum therefrom. Note that the burden rate "$\gamma(z_{nk})$" is given by the equation (6), and the effective value "$\pi_k^{new}$" is given by the equation (7).

$$\gamma(z_{nk}) = \frac{\pi_k N(x_n \mid \mu_k, \sigma_k)}{\sum_{j=1}^{K} \pi_j N(x_n \mid \mu_j, \sigma_j)} \quad (6)$$

$$\pi_k^{new} = \frac{N_k}{M} = \frac{\sum_{n=1}^{N} \gamma(z_{nk})}{M} \quad (7)$$

It is noted that "k" represents an index of the model distribution function (the normal distribution or the log normal distribution serving as a basis), and "K" represents its number. "$N_k$" represents an effective number of points assigned to the k-th cluster. The variable "$\pi_k$" is a weight of the k-th model distribution function, and a random value based on an appropriate ratio is used as the initial value of "$\pi_k$". "M" represents a number of samples.

The determination processing unit 324 determines whether or not the ratio of the objective cell to the objective cell groups, estimated by the estimation processing unit 323, satisfies a predetermined condition (e.g., equal to or larger than a constant value), and executes the pass determination processing of displaying the determination result on the display unit 340 in cooperation with the display control unit 350.

Specifically, in this embodiment, the determination processing unit 324 determines whether or not the ratio of the cell group serving as a target in the mixed distribution function generated by the generation processing unit 322, i.e., the skeletal myoblast, to the whole objective cell groups satisfies the predetermined condition (e.g., equal to or larger than a constant ratio). Then, the determination processing unit 324 determines "Passed" when the predetermined condition is satisfied, and determines "Failed" when the predetermined condition is not satisfied. The determination processing unit 324 displays the Result on the Display Unit 340.

[A4] Operation of Cell Quality Evaluation System

Figure 4:
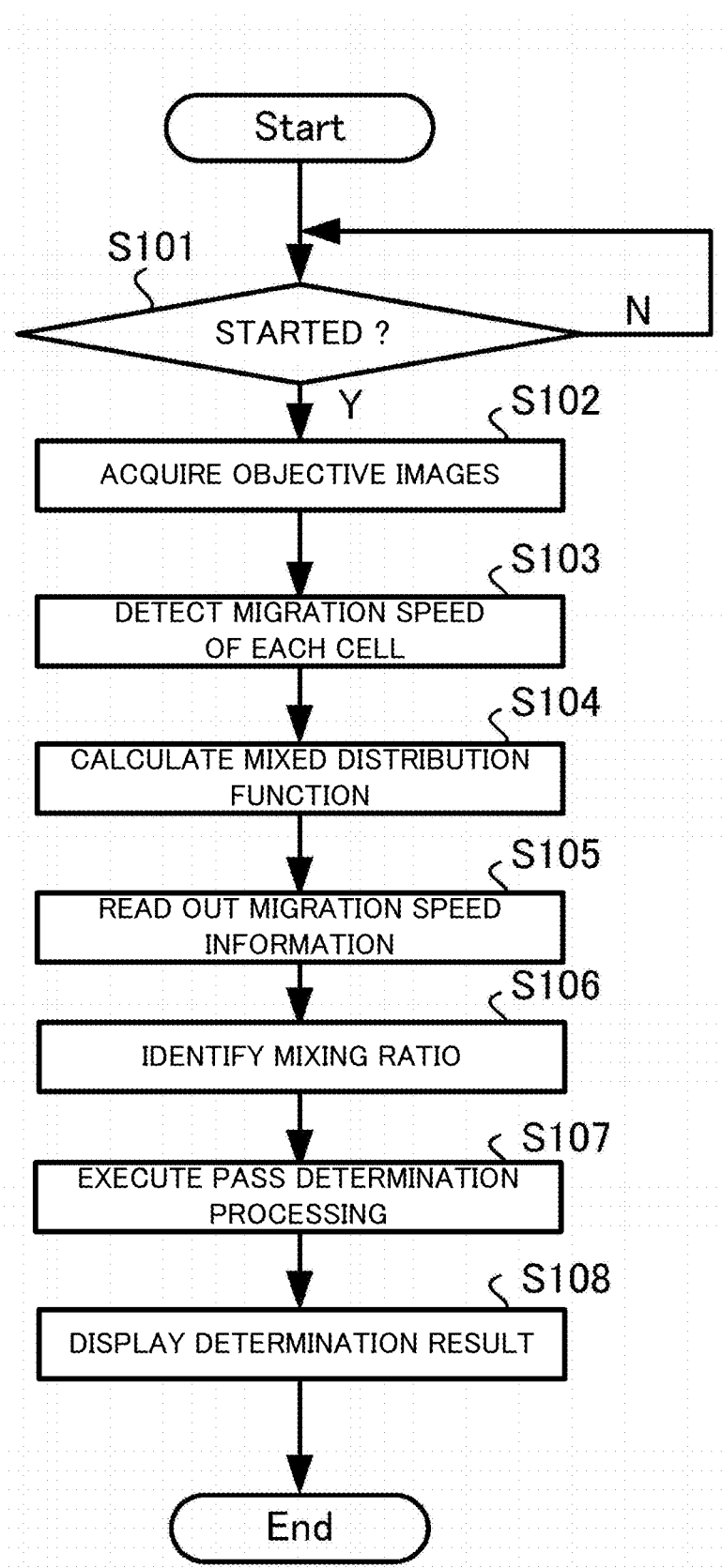
FIG. 4 is a flowchart illustrating an operation of quality determination processing executed by the image processing device according to the first embodiment.

Next, description will be given of the operation of the quality determination processing executed by the image processing device 30 of the cell quality evaluation system 1 according to this embodiment with reference to FIG. 4. FIG. 4 is a flowchart showing the operation of the quality determination processing executed by the image processing device 30 of the cell quality evaluation system 1 according to this embodiment.

In this operation, it is supposed that the data recording unit 300 stores, in advance, the plural objective image data acquired in time series and the migration speed information of the plural kinds of cell groups having different attributes and included in the objective cell groups of the objective images.

Also, in this operation, the migration speed detection processing is executed by an automatic tracking.

First, the detection processing unit 321 detects the start of the quality determination processing based on the operation to the operation unit 370 including selection of objective images (step S101), and acquires plural times-series objective images of specific objective cell groups selected (step S102).

Then, the detection processing unit 321 identifies the tracking of each cell included in the imaged objective cell groups, and detects the migration speed of each cell (step S103). Specifically, when the objective cell groups include 100 cells (or it is supposed that the objective cell groups include 100 cells), the detection processing unit 321 acquires the objective images of about 10 frames.

Next, the generation processing unit 322 calculates the average and the variance of the migration speed of each detected cell, and calculates the distribution function of the log normal distribution (the mixed distribution function) based on the averages and the variances thus calculated (step S104).

Next, the estimation processing unit 323 reads out the migration speed information (the averages and the variances) of the corresponding cell groups from the reference data recording unit 303 (step S105), and calculates the variable "$\pi$" of the mixing ratio satisfying the equations (3) and (4) based on the read-out migration speed information and the calculated mixed distribution function according to a predetermined algorithm to identify the ratio of the mixed distribution function (step S106).

Next, the determination processing unit 324 executes the pass determination processing which determines whether or not the ratio of the objective cell to the objective cell groups satisfies the predetermined condition (equal to or larger than a constant value) (step S107). Specifically, the determination processing unit 324 determines whether or not the predetermined condition is satisfied. The determination processing unit 324 determines "Passed" when the ratio of the objective cell to the objective cell groups satisfies the predetermined condition, and determines as "Failed" when the ratio does not satisfy the predetermined condition.

Finally, the determination processing unit 324 displays the determination result, i.e., the result of "Passed" or "Failed" on the display unit 340 in cooperation with the display control unit 350 (step S108), and ends the operation.

[A5] Simulation Results

[A5.1] Estimating Mixing Ratio

Figure 5A:
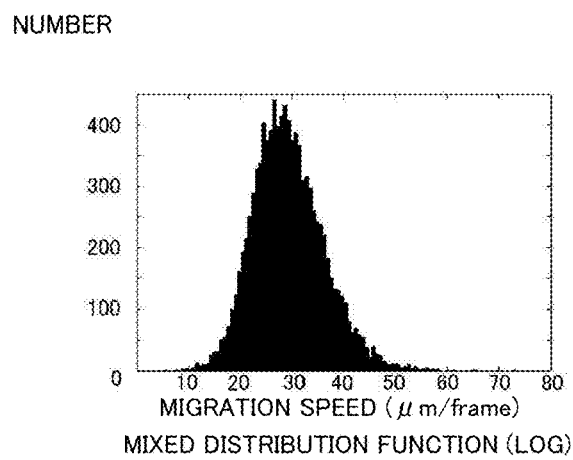
FIG. 5A is a diagram for explaining simulation (mixed distribution function) using a log function distribution in the first embodiment.
Figure 5B:
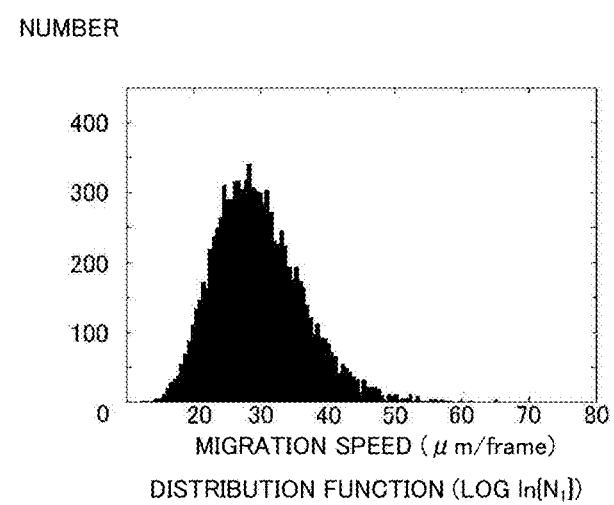
FIG. 5B is a diagram for explaining simulation (distribution function $N_1$) using a log function distribution in the first embodiment.
Figure 5C:
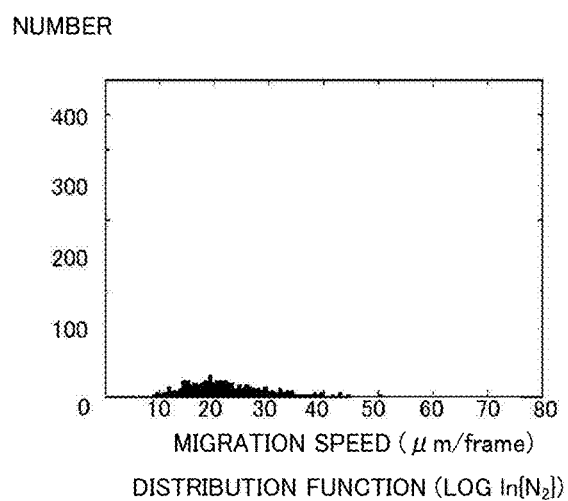
FIG. 5C is a diagram for explaining simulation (distribution function $N_2$) using a log function distribution in the first embodiment.

Next, simulation results of this embodiment will be described with reference to FIGS. 5A to 5C. FIGS. 5A to 5C are diagrams for explaining the simulation using the log distribution function according to this embodiment (the mixed distribution function, the distribution function $N_1$ or the distribution function $N_2$).

This simulation is executed in the objective cell groups including the skeletal myoblast and the fibroblast. Particularly, this simulation detects the migration speed of each cell mixed by a predetermined mixing ratio (i.e., the cell whose kind of the attribute is unknown), and estimates the mixing ratio of each cell group based on the detection result and the migration speed information of the skeletal myoblast and fibroblast detected in advance.

Specifically, in this simulation, the mixing ratio and the number of samples are changed, and the average error and the standard deviation are calculated when the simulation is carried out 100 times. Particularly, this simulation uses the result obtained by detecting the migration speeds of 100 cells per one frame. For example, when the number of samples is "1000", this simulation uses the result of detecting the migration speed of each cell for 10 frames, and calculates the ratio of the cell group of each cell species having different attributes by using the above-mentioned EM algorithm.

The simulation result using the normal distribution function is shown in TABLE-1, and the simulation result using the log normal distribution function is shown in TABLE-2 For example, as the simulation result using the normal distribution function, the distributions shown in FIGS. 3B and 3C are obtained for the mixed distribution shown in FIG. 3A. As the simulation result using the log normal distribution function, the distributions shown in FIGS. 5B and 5C are obtained for the mixed distribution shown in FIG. 5A.

In this simulation, as the migration speed information, the migration speed "$\mu_A$" is 29.72857 µm/frame and the variance "$\sigma_A$" is 60602264 for the skeletal myoblast, and the migration speed "$\mu_B$" is 22.5 µm/frame and the variance "$\sigma_B$" is 8.921323 for the fibroblast. This simulation is implemented without noise.

TABLE 1

| サンプル数 | 平均誤差 | 標準偏差 |
|---|---|---|
| 100 | 0.0735 | 0.0619 |
| 500 | 0.0332 | 0.0273 |
| 1000 | 0.0238 | 0.0152 |
| 5000 | 0.0204 | 0.0803 |
| 10000 | 0.009 | 0.0063 |

TABLE 2

| サンプル数 | 平均誤差 | 標準偏差 |
|---|---|---|
| 100 | 0.0439 | 0.0394 |
| 500 | 0.0220 | 0.0171 |
| 1000 | 0.0157 | 0.0139 |
| 5000 | 0.0073 | 0.0057 |
| 10000 | 0.0050 | 0.0040 |

As described above, when the normal distribution function is used, the maximum error is smaller than 7%, and it can be said that certain accuracy is ensured. Particularly, when the number of samples is larger than 1000, the error is smaller than 2.5%, and accuracy is sufficient.

When the log normal distribution function is used, accuracy is improved in all numbers of samples compared with the case of using the normal distribution function, and more favorable result is obtained. The reason is presumed as follows. In the normal distribution, for the movement distance used to calculate the migration speed of each cell, "minus" movement distances are allowed. On the other hand, in the log normal distribution, all the movement distances can be handled as "plus" movement distances, and this difference appears to be reflected to accuracy.

It is sufficient that the determination processing unit 324 in this embodiment determines whether or not the ratio of the objective cell to the objective cell groups, estimated in consideration that the above error is predicted, satisfies the predetermined condition (equal to or larger than a constant value). For example, when the error is predicted to be equal to or smaller than 2.5%, the determination processing unit 324 may determine the range within ±2.5% from the predetermined condition as a "Passed" range. However, since this "2.5%" is an average error, the "Passed" range may be broadened to ±3.0%, for example.

[A5.2] Noise Tolerance

Figure 6A:
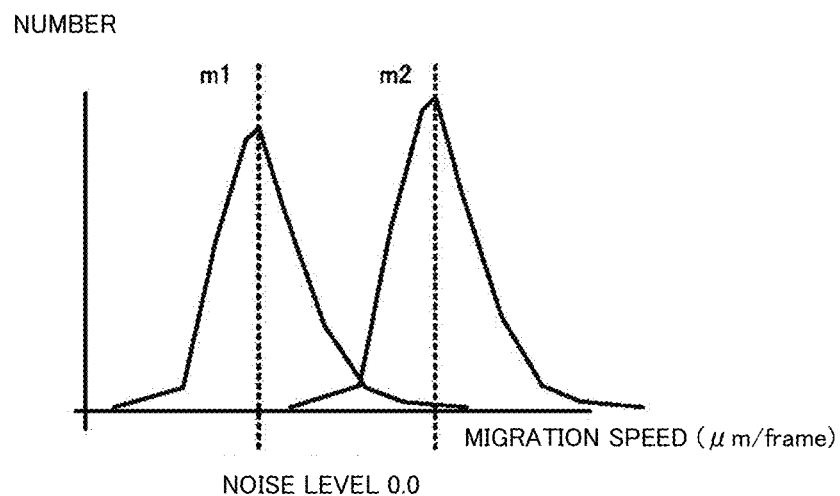
FIG. 6A is a diagram for explaining noise tolerance (noise level 0.0) in the first embodiment.
Figure 6B:
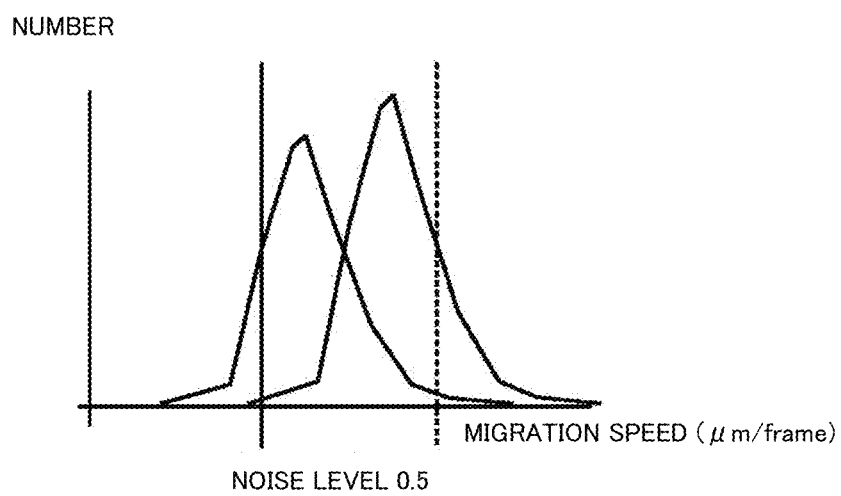
FIG. 6B is a diagram for explaining noise tolerance (noise level 0.5) in the first embodiment.
Figure 6C:
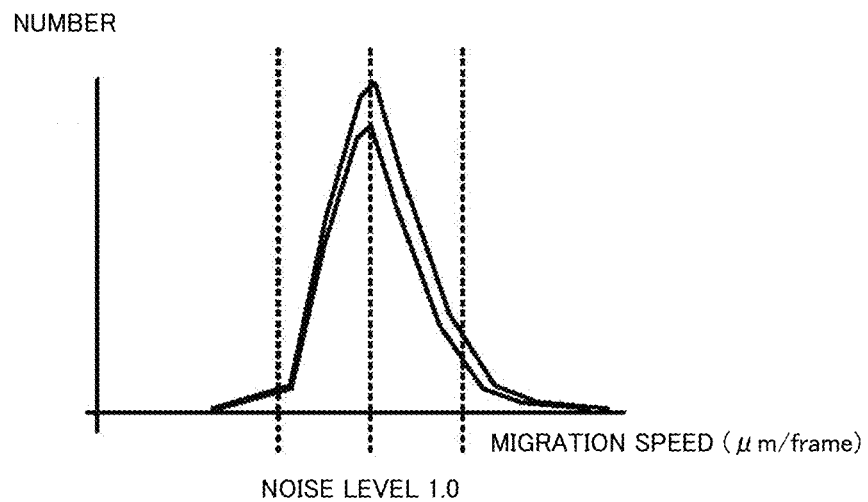
FIG. 6C is a diagram for explaining noise tolerance (noise level 1.0) in the first embodiment.
Figure 7:
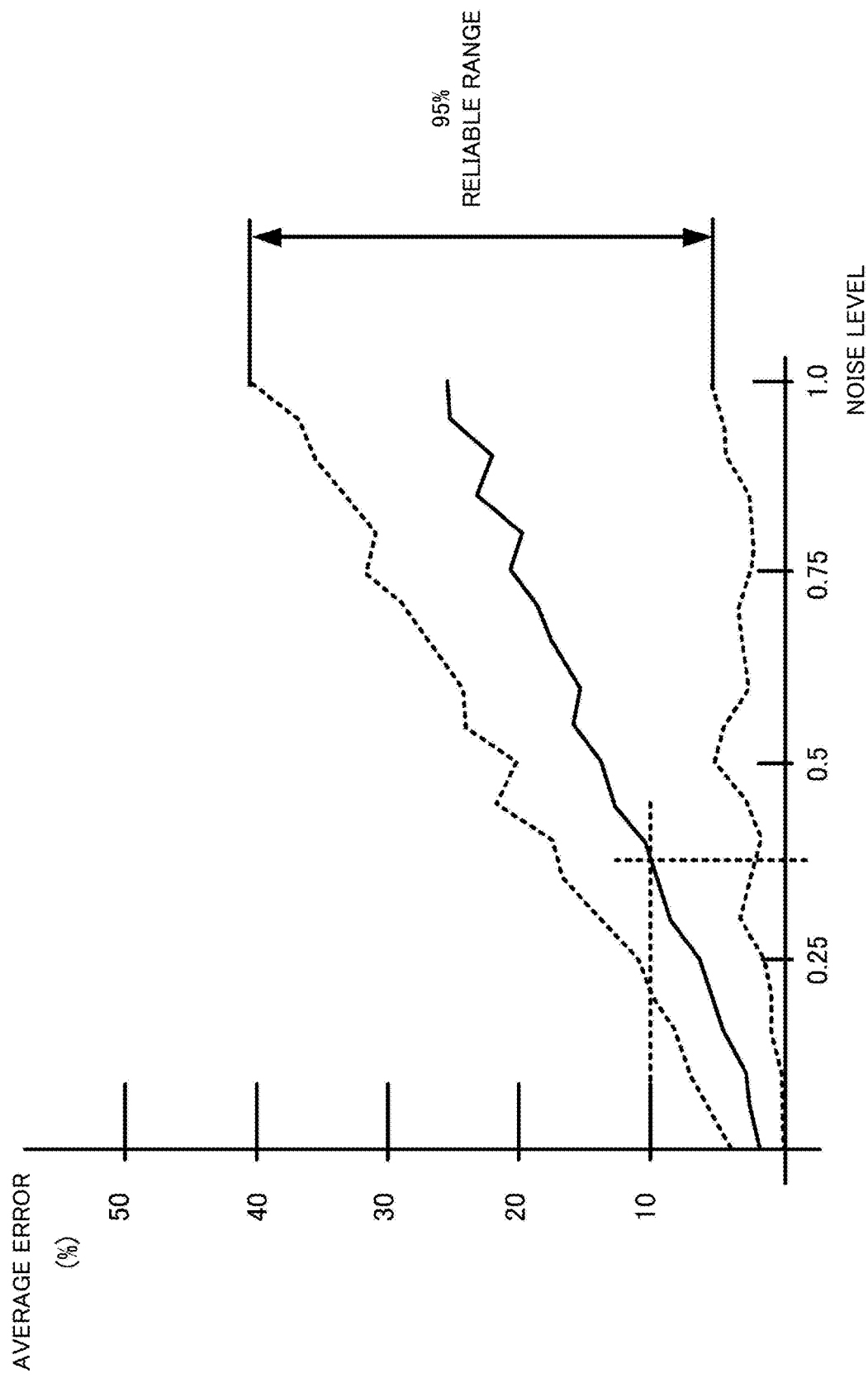
FIG. 7 is a graph illustrating a simulation result of an average error with respect to a noise level at an average migration speed in the first embodiment.

Next, description will be given of variation of estimation accuracy when noise exists in this embodiment, with reference to FIGS. 6A to 6C and FIG. 7. FIGS. 6A to 6C are diagrams for explaining noise tolerance (noise levels 0.0, 0.5 and 1.0) of this embodiment and FIG. 7 shows graphs illustrating simulation result of an average error with respect to the noise level at the average migration speed.

In this embodiment, it can be assumed that the donor of each cell to be detected in the objective cell groups is different from the donor of the pre-recorded migration speed information, that the migration speed itself is different due to a physical condition even if the donor of the pre-recorded migration speed information is identical to the donor from whom the objective cell is collected, or that the distribution ranges of the attribute (such as values) of mixed cells are largely overlapped.

Therefore, this simulation verifies the measurement errors in a case where noise is included in the migration speed of the cell to be actually detected and its distribution range (i.e., the average and the variance).

Specifically, similarly to the above-described simulation, this simulation is implemented for the objective cell groups including the skeletal myoblast and the fibroblast, and presents the result in a case where noise exists in each of the average migration speeds of the cell groups included in the objective cell groups.

Also, this simulation defines the noise level by the equation (8). Particularly, as shown in FIG. 6A, when the noise level "L" is "0.0", the averages of the migration speeds of the skeletal myoblast and the fibroblast actually included in the objective cell groups coincide. As shown in FIG. 6B, when the noise level "L" is "0.5", the difference of the averages become a half of the difference value in this embodiment. As shown in FIG. 6C, when the noise level "L" is "1.0", there is a difference of normal value for the averages of the migration speeds.

$$\frac{m1 - m2}{2} \times L \qquad (8)$$

As the supposed migration speeds, as described above, the migration speed "$\mu_A$" is m1=29.72857 μm/frame and the variance "$\sigma_A$" is 60602264 for the skeletal myoblast, and the migration speed "$\mu_B$" is m2=22.5 μm/frame and the variance "$\sigma_B$" is 8.921323 for the fibroblast.

Also, in this simulation, for each noise level L from "0" to "1.0" by "0.05" interval, the number of samples (1000 samples) is fixed and the mixing ratio is varied. The simulation is implemented 100 times with adding the noise based on the equation (8) using the above-mentioned EM algorithm, and the average errors at the mixing ratios are obtained.

FIG. 7 illustrates result of this simulation in the migration speed and the average error. If the average error is smaller than 10%, it can be said that accuracy is ensured. As the noise level satisfying the reliable range (95%), the noise level up to about "0.2" is within an allowable range.

Thus, even if there occurs various noises such as the difference of donors or physical condition of the donors, if the noise is smaller than a constant noise level, it is possible to estimate the mixing ratio in the objective cell groups.

[A6] Modified Examples

[A6.1] 1st Modified Example

In the above embodiment, the imaging device 10 and the image processing device 30 may be placed or used in the same room or in the same site. Instead, each of the imaging device 10 and the image processing device 30 may be placed or used at remote places such as foreign countries to implement the above-described processing.

The image processing device 30 may execute the quality determination processing using a database connected via the network 20, or may be formed by one or plural devices. When the database is used, the database performs a part of the function of the data recording unit 300 (e.g., recording the objective images or the migration speed information).

[A6.2] 2nd Modified Example

In the above embodiment, the cell quality evaluation system is formed by the imaging device 10 and the image processing device 30. However, the cell quality evaluation system of stand-alone type may be realized by providing an image data generation unit including a scanner and an imaging function. In that case, the image data generation unit constitutes the acquisition unit of the present invention, for example.

[A6.3] 3rd Modified Example

The above embodiment estimates the mixing ratios of the two kinds of objective cell groups such as the skeletal myoblast and the fibroblast. However, the present invention is applicable to the objective cell groups in which plural cell groups having different attributes of three or more kinds are mixed.

[A6.4] 4th Modified Example

In the above embodiment, the EM algorithm is used to calculate the ratio of the mixed distribution function. However, it may be solved as a least squares method problem with constraint conditions, without calculating the mixed distribution function of the detected migration speed of each cell.

For example, as a least squares method problem with constraint conditions, it is possible to assume that the mixed distribution is a sum of weights (i.e., $\pi_A$ and $\pi_B$) of basic distributions (i.e., the distribution A of the skeletal myoblast and the distribution B of the fibroblast in the above embodiment), as a histogram having predetermined number of bins. Therefore, the mixed distribution "S" and the basic distributions "A" and "B" may be expressed by p-dimensional vector when the number of bins is "q", and it is possible to calculate the ratio (i.e., $\pi_A$ and $\pi_B$) with which "P" in the equation (10) becomes minimum based on the equation (9).

Namely, while the problem of calculating the weights $\pi_A$ and $\pi_B$ to achieve the equation (9) is considered, coincident value does not necessarily exists. Therefore, the weights are estimated by solving the problem of satisfying the constraint that the weights are positive and the sum of the weights is 1 and making the square error between the observed distribution S and the estimated combined distribution ($\pi_A A + \pi_B B$) becomes minimum.

$$S = x_q(q = 1, \ldots, Q) = (AB)\begin{pmatrix} \pi_A \\ \pi_B \end{pmatrix} = \pi_A A + \pi_B B \quad (9)$$

$$0 < \pi_A, \pi_B < 1, \pi_A + \pi_B = 1$$

$$\min P = \min_{\pi_A, \pi_B} \frac{1}{2}\|S - (\pi_A A + \pi_B B)\| \text{ s.t.} \quad (10)$$

$$(0 \le \pi_A, \pi_A \le 1, \pi_A + \pi_A = 1$$

[A6.5] 5th Modified Example

The detection processing unit 321 in the above embodiment detects the migration speed of the cells of 1000 samples. This may be achieved by making the imaging time long and sampling an arbitrary one point of the dish in the time-lapse image (temporal sampling), or by using arbitrary plural points in the time-lapse image as the samples (spatial sampling). Also, in the detection processing unit 321, the temporal sampling and the spatial sampling may be combined.

[A6.6] 6th Modified Example

In the above embodiment, the mixing ratio of each of the plural kinds of cell groups is estimated using the normal distribution and the log normal distribution. However, other probability distribution function such as gamma distribution or beta distribution to be fit to the cell migration speed distribution may be used.

As described above, when cell species other than certain cell species to be used is mixed into the objective cell groups, the cell quality evaluation system of this embodiment can perform the quality evaluation of the objective cell groups, e.g., the calculation of purity of certain cell species included in the objective cell groups, by estimating the ratio of the certain cell species using the images. Also, the cell quality evaluation system of this embodiment can evaluate the culture state of the objective cell groups during or after the culture, e.g., cell death of certain cell species or mutation to other cell species during the culture. Therefore, not only the quality control of the objective cell groups and the certain cell species, but also the production control of the cell species can be easily and accurately performed.

[B] 2nd Embodiment

[B1] Outline of Culture Management System

First, an outline of a culture management system 2 according to a second embodiment will be described.

The culture management system 2 of this embodiment manages a state of the objective cell groups including plural kinds of cell groups having different attributes in a predetermined culture period using the cell quality evaluation system 1 of the first embodiment.

Specifically, the culture management system 2 of this embodiment uses the imaging device 10 and the image processing device 30 in the first embodiment, and manages culture of the objective cell groups including plural kinds of cell groups having different attributes such that the cell group (e.g., fibroblasts) other than the specific cell group to be used (e.g., skeletal myoblasts) is not cultured more than a prescribed degree, e.g., the degree of disabling its use for regenerative medicine, in the objective cell groups in the culture period.

Also, the culture management system 2 in this embodiment has such a characteristic point that it executes, in the first embodiment, determination processing of determining whether or not the mixing ratios of the plural kinds of cell groups satisfy the predetermined mixing ratio condition and notification processing of notifying the result of the determination processing to a manager at a predetermined timing or at every predetermined timing in the culture period.

It is noted that this embodiment has the same configuration as the first embodiment except for the above-described characteristic point. The same elements are denoted by the same reference numbers, and the description therefore will be omitted.

[B2] Configuration of Culture Management System

Figure 8:
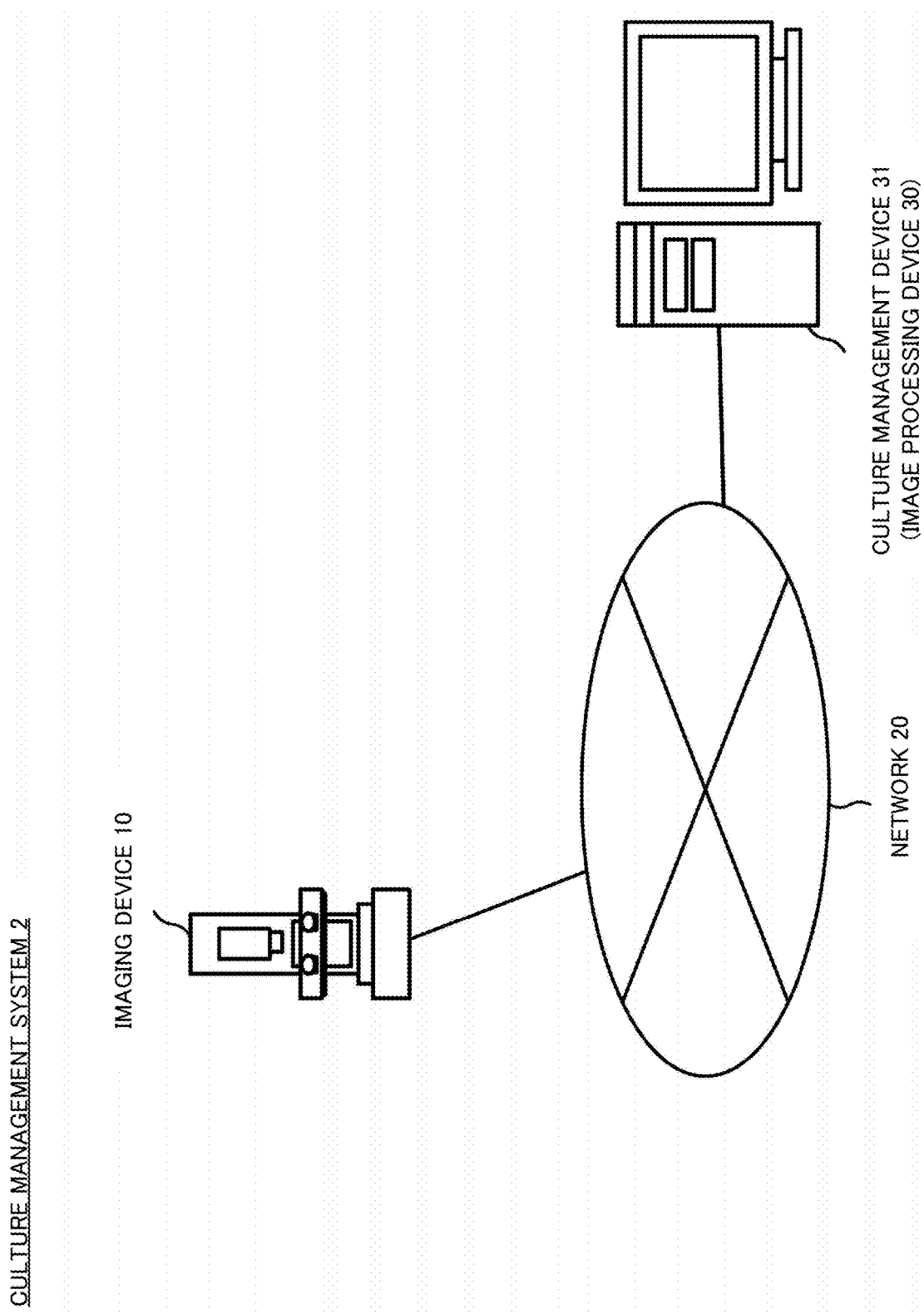
FIG. 8 is a diagram illustrating a configuration of a culture management system according to a second embodiment of the present invention.

Next, a configuration of the culture management system 2 according to the second embodiment will be described with reference to FIG. 8. FIG. 8 is a system configuration diagram illustrating the configuration of the culture management system 2 of this embodiment.

The culture management system 2 of this embodiment includes the imaging device 10 which images the objective cell groups in time series and generates the objective image data, the network 20, and a culture management device 31 which executes the culture management of the objective cell groups during the culture period.

The culture management device 31 has the same functions as the image processing device 30 of the first embodiment, and additionally has functions of determining whether or not the mixing ratios of the plural kinds of cell groups in the objective cell groups satisfy the mixing ratio condition at every predetermined timing in the predetermined culture period and executing a predetermined notification of the determination result to the manager.

Namely, as the same functions as the image processing device 30 of the first embodiment, in cooperation with the imaging device 10, the culture management device 31 analyses the objective image data generated by the imaging device 10 to estimate the mixing ratios of the plural kinds of cell groups, and evaluates the quality of the objective cell groups based on the estimated mixing ratios.

Specifically, similarly to the image processing device 30 of the first embodiment, the culture management device 31 executes processing of:

(1) acquiring plural objective images of the objective cell groups from the imaging device 10 in time series during a predetermined culture period, (2) detecting a migration speed of each cell in the objective images by analyzing the acquired plural objective images, (3) generating a distribution function or a distribution state of the migration speeds of the imaged objective cell groups based on the detected migration speed of each cell, (4) estimating a mixing ratio of each of the plural kinds of cell groups based on the pre-recorded migration speed information indicating the migration speed of each of the plural kinds of cell groups and the generated distribution function or the generated distribution state, and (5) determining the quality of the objective cell groups as "Passed" when the estimated mixing ratios satisfy the predetermined condition.

On the other hand, the culture management device 31 of this embodiment executes the determination processing at predetermined timings (particularly, at every predetermined timing) in the culture period, and executes the predetermined notification to the manager when the mixing ratios of the plural kinds of cell groups satisfy the mixing ratio condition in the determination result.

As described above, in case of culturing cells (e.g., skeletal myoblasts) collected from a living body and using the cultured cells for treatments such as regenerative medicine, it is necessary to ensure the quality higher than a certain degree. On the other hand, in the first place, collecting cells from the living body causes an influence to the living body and hence the cells cannot be repeatedly collected. Therefore, it is also necessary to improve the quality of the cells to a usable level to avoid destroying the collected cells for the reason that the quality is not sufficient.

Particularly, when cells of a patient himself who receives regenerative medicine (autologous cell) are collected and cultured as the objective cell groups, it is desired to ensure the quality of all the objective cell groups and to use all of them in treatment.

Therefore, in this embodiment, the above-described determination processing is executed at every predetermined timing in the culture period to determine the quality of the objective cell groups periodically in the culture period, and the manager is notified whether the quality is maintained or degraded, for example.

Particularly, in this embodiment, by executing such notification, it becomes possible to urge the manager to execute predetermined processing, for example, to remove (or kill) unnecessary cell species to prevent further proliferation for the objective cell groups including plural cell species having different doubling times.

With the above configuration, in this embodiment, by notifying the condition of the objective cell groups such as the quality of the objective cell groups during culture, it becomes possible to manage the culture of the objective cell groups including plural kinds of cell groups having different attributes, so as to prevent that cell species other than the specific cell species to be used are cultured in the objective cell groups more than a prescribed degree during the culture period and the cell species in the objective cell groups becomes unusable for regenerative medicine, for example.

Particularly, in this embodiment, in case of the objective cell groups including cell groups of plural kinds of cell species having different doubling times, such as the objective cell groups collected from a living body (specifically muscle fibers) formed by the skeletal myoblasts and the fibroblasts, it is possible to continue the culture of the cell groups of necessary cell species such as the skeletal myoblasts, while preventing the culture of the cell groups of unnecessary cell species such as the fibroblasts. Therefore, it becomes possible to culture useful objective cell groups including necessary cell species with a high mixing ratio.

Accordingly, this embodiment can perform quality control of the objective cell groups during the culture, and make the manager to control the culture of the objective cell groups while performing the quality control, thereby improving production efficiency of the objective cell groups.

Figure 9:
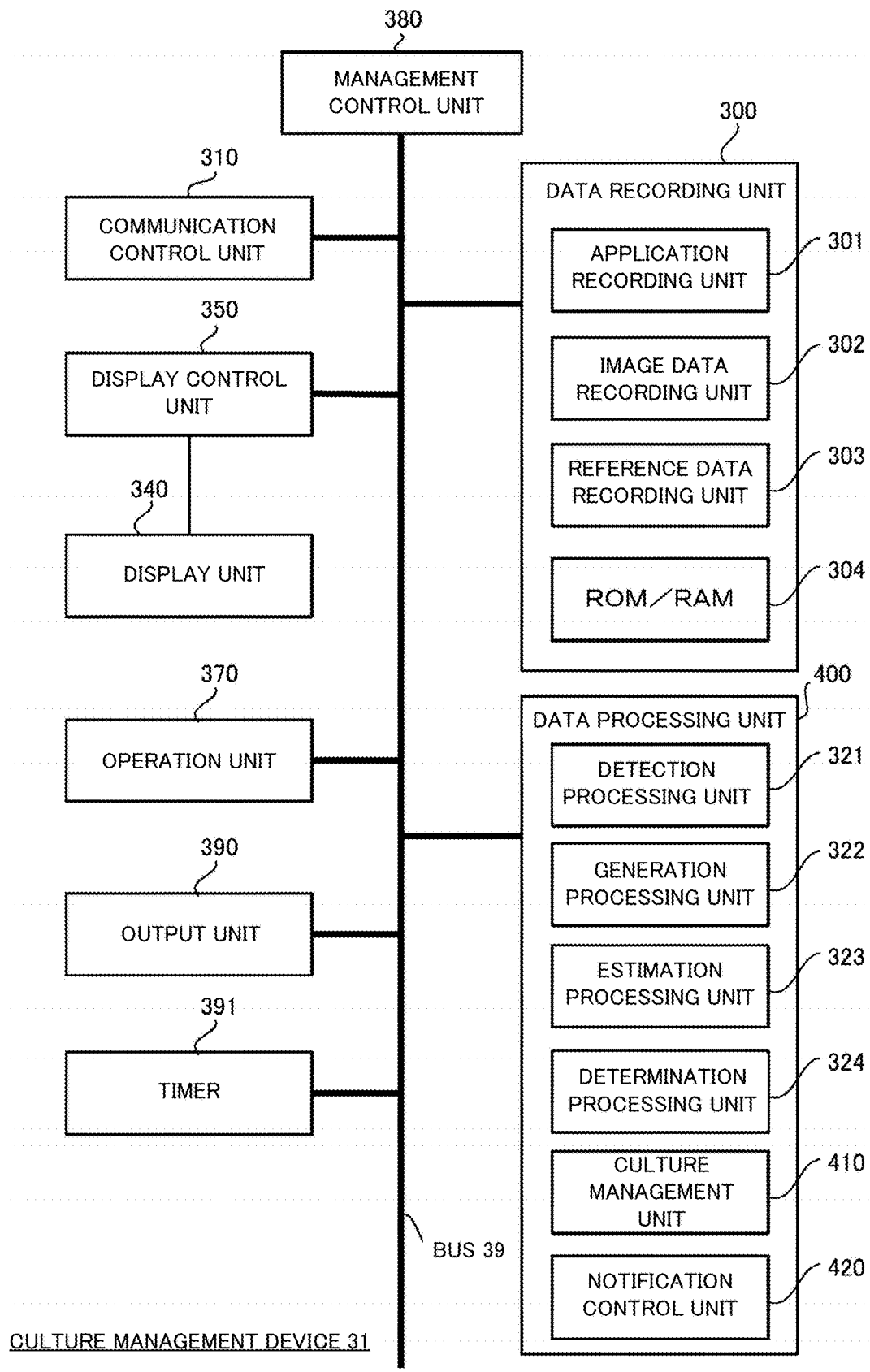
FIG. 9 is a block diagram illustrating a configuration of an image processing device of the culture management system according to the second embodiment.

Next, a configuration of the culture management system 31 of this embodiment will be described with reference to FIG. 9. FIG. 9 is a block diagram illustrating blocks of the culture management device 31 of this embodiment.

As shown in FIG. 9, the culture management device 31 of this embodiment includes a data recording unit 300, a communication control unit 310, a display unit 340, a display control unit 350, an operation unit 370 and a management control unit 380. Further, the culture management device 31 includes an output unit 390 which performs a predetermined notification to the manager, a timer 391, and a data processing unit 400 which executes quality determination processing based on the generated objective images and culture management. The above blocks are connected with each other via a bus 39 to execute data transfer between the blocks.

The data processing unit 400 of this embodiment constitutes a notification control unit of the present invention, and the output unit 390 constitutes an output unit of the present invention.

The output unit 390 is a device, such as a speaker, an alarm or a lamp, which notifies the manager of an abnormality of the objective cell groups by sounds or lights during the culture management.

Specifically, the output unit 390 notifies the determination result of the determination processing executed at a predetermined timing or at every predetermined timing in the predetermined culture period.

For example, when the mixing ratio of each of the plural kinds of cell groups satisfies the mixing ratio condition, the output unit 390 outputs a notification indicating that the condition is satisfied or that the culture can be continued, to the manager by a display, sounds or lights.

Also, when the mixing ratio of each of the plural kinds of cell groups does not satisfy the mixing ratio condition, the output unit 390 outputs, to the manager, a notification indicating that the condition is not satisfied or that the culture cannot be continued and certain processing is needed (e.g., processing to suppress culture of unnecessary cell species, such as killing) to the manager by a display, sounds or lights.

In this embodiment a predetermined image may be displayed on the display unit 340 to make the display unit 340 function as an output unit for performing notification to the manager.

The timer 391 outputs a date and a time (a current time) based on the instruction by the data processing unit 400, or counts time to make an output when a predetermined timing arrives.

Similarly to the first embodiment, in order to execute the migration speed detection processing, the distribution function generation processing, the mixing ratio estimation processing and the pass determination processing, the data processing unit 400 executes applications for the quality determination processing recorded in the ROM/RAM 304 to realize the detection processing unit 321, the generation processing unit 322, the estimation processing unit 323 and the determination processing unit 324.

Also, the data processing unit 400 realizes the culture management unit 410 and the notification control unit 420 by executing applications.

The culture management unit 410 controls each block at a predetermined timing (or at every predetermined timing) in the culture period, and executes the migration speed detection processing, the distribution function generation processing, the mixing ratio estimation processing and the pass determination processing thereby to acquire the pass determination result.

Also, when the culture management unit 410 executes the pass determination processing at every predetermined timing, it changes the mixing ratio condition at every timing.

Particularly, the culture management unit 410 uses stricter mixing ratio condition in the determination processing at a timing of a short elapsed time in the culture period, than the mixing ratio condition in the determination processing at a timing of a long elapsed time.

For example, similarly to the first embodiment, for the objective cell groups including two cell species of the skeletal myoblasts and the fibroblasts, the culture management unit 410 determines whether or not the ratio to the (whole) objective cell groups satisfies a predetermined condition (e.g., equal to or larger than a constant value) at every predetermined timing such as a culture exchange timing or a subculture timing in the culture period (specifically, primary culture and each subculture is one week) including primary culture and subculture (extended culture).

Also, when extended culture is performed N times and the mixing ratio of the necessary cell species (i.e., the skeletal myoblast) for use in regenerative medicine to the whole objective cell groups is equal to or larger than a predetermined ratio (e.g., a minimum ratio usable for regenerative medicine, specifically more than twice the number of cells necessary for transplanting), the culture management unit 410 uses the mixing ratio condition that the mixing ratio of the necessary cell species (e.g., the skeletal myoblast) to the whole objective cell groups is 95% for the (N−2)th extended culture in the culture period (e.g., (N+1) week), and uses the mixing ratio condition that the mixing ratio of the necessary cell species (e.g., the skeletal myoblast) to the whole objective cell groups is 90% for the (N−1)th extended culture.

Of course, in the above case, for the Nth extended culture, the culture management unit 410 uses the mixing ratio condition that the mixing ratio of the necessary cell species (e.g., the skeletal myoblast) to the whole objective cell groups is equal to or larger than a predetermined ratio.

Then, the culture management unit 410 acquires the result of the determination processing based on the mixing ratio condition.

In the above example, when the subculture is executed N times, the mixing ratio condition is changed in the determination processing after the (N−2)th and (N−1)th subcultures. However, the mixing ratio condition may be changed in the primary culture and each of the subcultures, or a constant condition may be used without changing the mixing ratio condition.

Also, in this embodiment, the determination processing may be executed for each of the primary culture and the subcultures. Alternatively, the determination processing may be executed during and/or after the primary culture, or during and/or after the subculture.

The notification control unit 420 controls the output unit 390 after execution of each determination processing or at a predetermined timing (a timing requested by the manager or after the final determination processing) based on the determination result of each determination processing acquired by the culture management unit 410, and makes the output unit 390 execute the predetermined notification to the manager.

In the first embodiment, the determination processing unit 324 controls the display control unit 350 to display the determination result on the display unit 340. The notification control unit 420 of this embodiment may control the display control unit 350 to display an image for executing a predetermined notification on the display unit 340.

[B4] Operation of Culture Management System

Figure 10:
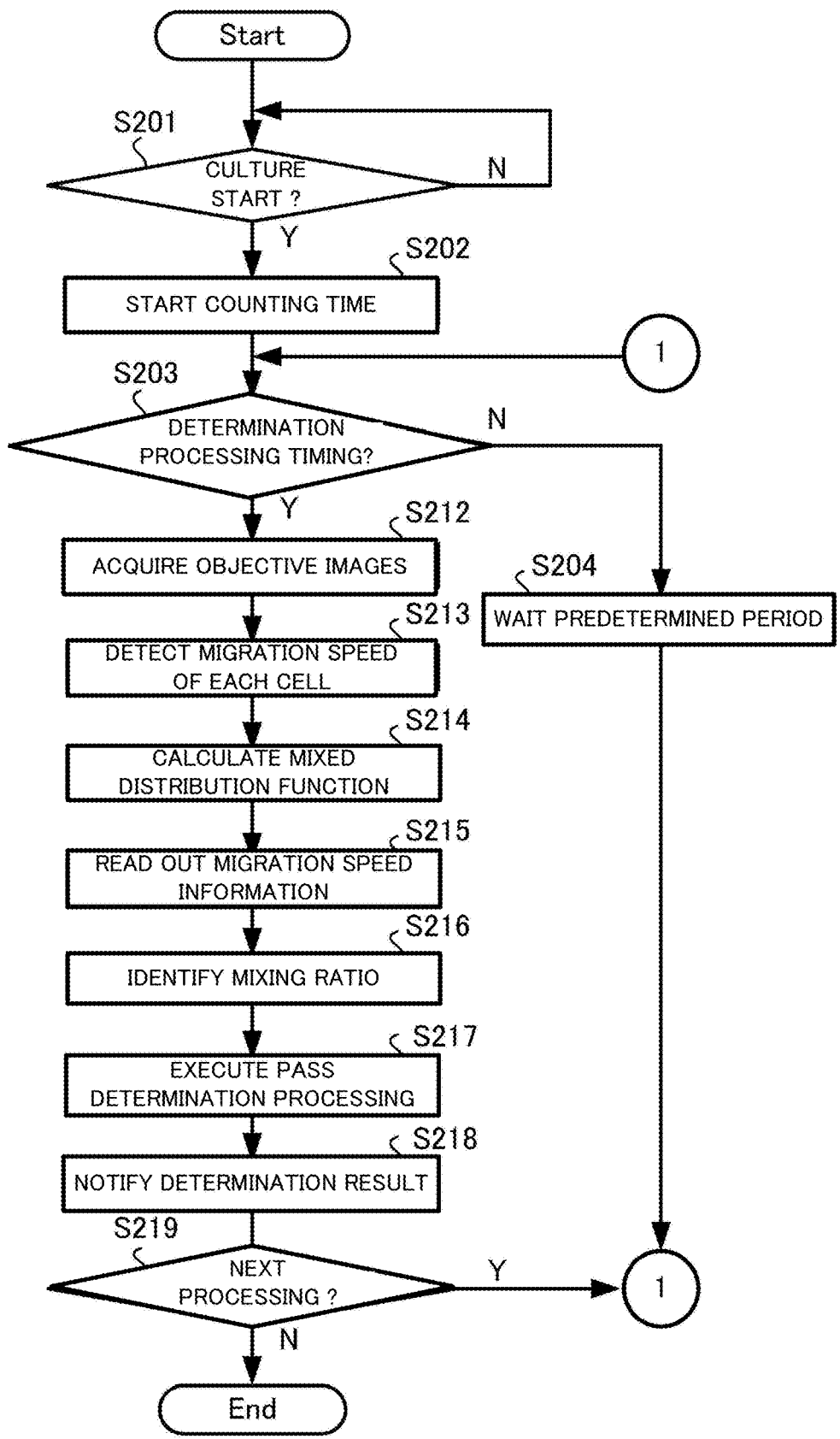
FIG. 10 is a flowchart illustrating an operation of culture management processing executed by the culture management device according to the second embodiment.

Next, a description will be given of an operation of the culture management processing executed by the culture management device 31 of the culture management system 2 according to this embodiment with reference to FIG. 10. FIG. 10 is a flowchart illustrating the operation of the culture management processing executed by the culture management device 31 of the culture management system 2 according to this embodiment.

In this operation, it is supposed that the determination processing is executed at every timing in the culture period, and a predetermined notification is made to the manager as a warning when the mixing ratio condition in each determination processing is not satisfied.

Also, in this operation, it is supposed that the culture of the objective cell groups is performed in a predetermined dish set in an incubator not shown, and it is supposed that the objective images of the objective cell groups are generated by the imaging device 10 at predetermined timings in the culture, acquired in time series and recorded in the data recording unit 300.

Also, in this operation, the migration speed information of the plural kinds of cell groups having different attributes included in the objective cell groups of the objective image are recorded in the data recording unit 300 in advance.

Further, in this operation, the migration speed detection processing is executed by an automatic tracking.

First, when the culture management unit 410 detects the start of the culture period based on the operation by the manager (step S201), it makes the timer 391 start counting time (step S202).

Next, the culture management unit 410 makes the timer 391 determine whether or not the current time is the timing to execute the determination processing (step S203). If the timer determines that the current time is the timing to execute the determination processing, the processing moves to step S212. If the timer 391 determines that the current time is not the timing to execute the determination processing, the culture management unit 410 waits for a predetermined time period (step S204), and returns to step S203.

Next, if the timer 391 determines that the current time is the timing to execute the determination processing, the culture management unit 410 selects the objective images of the objective cell groups (i.e., a specific objective cell groups) on the dish based on the operation to the operation unit 370, and acquires plural time-series objective images of the certain objective cell groups thus selected (step S212).

Next, the detection processing unit 321 identifies tracking of each cell included in the imaged objective cell groups and detects the migration speed of each cell (step S213). Specifically, when the objective cell groups include 100 cells (or it is supposed that the objective cell groups include about 100 cells), the detection processing unit 321 acquires the objective image of about 10 frames.

Next, the generation processing unit 322 calculates an average and a variance of the migration speed of each detected cell, and calculates the distribution function (the mixed distribution function) of the log normal deviation based on the average and the variance thus calculated (step S214).

Next, the estimation processing unit 323 reads out the migration speed information (the average and the variation) of the corresponding cell group from the reference data recording unit 303 (step S215), and calculates the variable "π" of the mixing ratio satisfying the equations (3) and (4) according to a predetermined algorithm based on the read-out migration speed information and the calculated mixed distribution function, thereby to identify the ratio of the mixed distribution function (step S216).

Next, the determination processing unit 324 executes the pass determination processing which determines whether or not the ratio of the objective cell to the objective cell groups satisfies the predetermined condition (equal to or larger than a constant value) (step S217). Specifically, the determination processing unit 324 determines whether or not the predetermined condition is satisfied. At that time, the determination processing unit 324 determines "Passed" when the ratio of the objective cell to the objective cell groups satisfies the predetermined condition, and determines "Failed" when the ratio does not satisfy the predetermined condition.

Next, in cooperation with the display control unit 350, the notification control unit 420 makes the display unit 340 and the output unit 390 output the determination result, i.e., the result of Passed or Failed, to be notified to the manager (step S218).

When the mixing ratio of the objective cell to the objective cell groups does not satisfy the predetermined condition, the culture management unit 410 urges to execute predetermined processing, e.g., processing to kill the cell species other than the objective cell.

When the mixing ratio of the objective cell with respect to the objective cell groups does not satisfy the predetermined condition, the culture management unit 410 may stop the culture of the objective cell and forcedly terminate this operation.

Finally, the culture management unit 410 determines whether or not next determination processing exists (step S219). When it is determined that the next determination processing exists, the culture management unit 410 moves to step S203. When it is determined that the next determination processing does not exist (i.e., the processing in the previous step S217 is the final determination processing), the culture management unit 410 ends this operation.

[C] 3rd Embodiment

[C1] Outline of Cell Group Production Method

Next, description will be given of an outline and an operation principle of a cell group production method according to the third embodiment.

The cell group production method of the this embodiment produces at least specific kinds of cell groups by controlling the culture in a predetermined culture period for the objective cell groups collected from a living body and including plural kinds of cell groups having different attributes.

The cell group production method of the this embodiment uses the culture management system 2 including the culture management device 31 having a culture inhibition function described later. When the objective cell groups are usable after the predetermined culture period, the cell group production method executes process for executing predetermined processing, such as cryopreservation and standard test, for using the objective cell groups to the living body.

Specifically, the cell group production method executes:

(A) inspection processing including at least the determination processing of determining whether or not the mixing ratio of each of the plural kinds of cell groups included in the objective cell groups to the cultured objective cell groups satisfies the predetermined mixing ratio condition at predetermined timings in the predetermined period by using the culture management system 2, and (B) inhibition processing of inhibiting culture of unnecessary cell species in the objective cell groups or preparation processing for executing the inhibition processing, when the determination processing determines that the mixing ratio of each of the plural kinds of cell groups does not satisfy the mixing ratio condition.

In the cell group production method of the this embodiment, as the inspection processing of (A), similarly to the second embodiment, the culture management system 2:

(A1) acquires a plurality of objective image data of the objective cell groups in time series at a predetermined timing (or at every predetermined timing), (A2) detects the migration speed of each cell imaged in the objective image by analyzing the plurality of acquired objective image data, (A3) generates the distribution function or the distribution state of the migration speeds of the imaged objective cell groups based on the detected migration speed of each cell, and (A4) estimates the mixing ratio of each of the plural kinds of cell groups included in the objective cell groups to execute the determination processing based on the mixing ratio condition, on the basis of the migration speed information recorded in the database and including information of the migration speed of each of the plural kinds of cell groups, and the generated distribution function or the generated distribution state.

Also, in the cell group production method of the this embodiment, as the processing (B), the culture management system 2 executes (B1) the inhibition processing of inhibiting the culture of unnecessary cell species in the objective cell groups so as to stop the proliferation of the unnecessary cell species (including killing), or (B2) the preparation processing for executing the inhibition processing such as urging the manager to execute the inhibition processing.

Then, in the cell group production method of the this embodiment, when the mixing ratio of each of the plural kinds of cell groups satisfies the mixing ratio condition (e.g., the ratio of the cell group of necessary cell species to the objective cell groups is equal to or larger than a predetermined ratio) in the determination processing at the ending time of the culture period, it is determined that the objective cell groups are usable and pass the final inspection processing.

On the other hand, in the cell group production method of the this embodiment, when it is determined in the final inspection processing that the objective cell groups are usable, cryopreservation is performed before the use timing. At the use timing, a final use determination is executed by the specification testing. When the objective cell groups pass the specification testing, it is processed to a use form such as a cell sheet.

In the this embodiment, with the above configuration, when the cell species other than specific cell species (e.g., skeletal myoblast) to be used is mixed in the objective cell groups for example, the culture of the objective cell groups during the culture (i.e., the mixing ratio of the plural kinds of cell species in the objective cell groups) may be controlled.

Namely, in the this embodiment, when the mixing ratio of the unnecessary cell species in the objective cell groups becomes larger than a specified ratio, it does not pass the inspection processing, and hence it becomes possible to stop the use of the objective cell groups having low quality. Additionally, since the mixing ratio can be controlled by inhibiting the culture of the unnecessary cell species in the objective cell groups after the inspection processing, it becomes possible to make the objective cell groups finally pass the inspection processing.

Accordingly, in the this embodiment, it is possible to culture and produce the objective cell groups of proper quality and to improve production efficiency of the objective cell groups.

In the third embodiment, it is supposed that the culture management device 31 has a culture inhibition function.

In the cell group production method of the this embodiment, the culture management device 31 of the culture management system 2 may have the culture function, or the culture management system 2 may have the culture device (not shown) separately from the culture management device 31.

For example, the culture device (the culture management device 31) maintains its inside atmosphere to satisfy a predetermined environmental condition, and includes a thermostatic chamber capable of housing a plurality of culture containers for culturing cells and an imaging unit which generates the images of the cultured cells as described in the first embodiment.

[C2] Principle of Cell Group Production Method

Next, the principle of the cell group production method according to the third embodiment will be described with reference to FIGS. 11, 12A and 12B.

Figure 11:
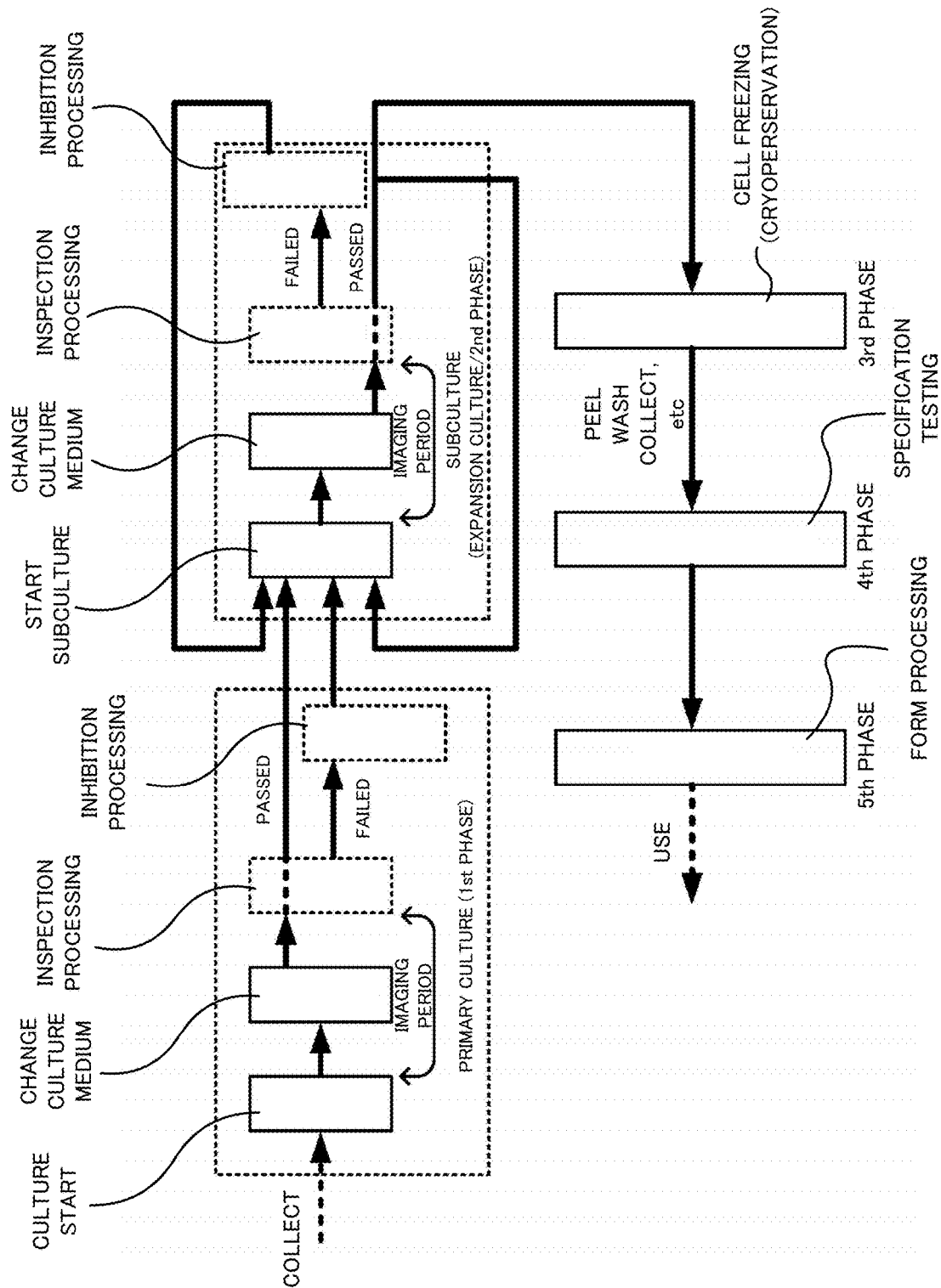
FIG. 11 is a diagram for explaining a principle of a cell production method according to a third embodiment of the present invention.

FIG. 11 is a diagram for explaining the principle of the cell group production method according to this embodiment. FIGS. 12A and 12B are diagrams illustrating identifying the fibroblasts from the image of the objective cell groups in which the fibroblasts and the skeletal myoblasts are mixed in the third embodiment. FIG. 12A is a diagram illustrating a phase contrast image of the objective cell groups of a mouse imaged by a phase contrast microscope, and FIG. 12B is a diagram illustrating an image of the objective cell groups of FIG. 12A in which the fibroblasts are fluorescently dyed.

First, the objective cell groups collected from a living body is put in a dish in which a specified culture medium is placed, and the culture (the primary culture) is started. The culture is performed a predetermined period (e.g., 7 days) (the first phase in FIG. 11).

At that time, the culture management device 31 starts the culture management based on the operation by the manager, and manages the dish in which the culture is started in an incubator. During the primary culture, the culture medium is exchanged at a predetermined timing (e.g., 4th day from the start of the primary culture).

Next, when the primary culture ends, the subculture is performed N times (N: natural number) in which the objective cell is separated and cultured (the second phase in FIG. 11).

At that time, the culture management device 31 executes the culture management based on the operation of the manager, and manages the dishes in which the objective cell groups are cultured in the incubator similarly to the primary culture. Similarly to the primary culture, the culture medium is exchanged at a predetermined timing (e.g., 4th day from the start of the primary culture) in each of the subcultures.

On the other hand, during the primary culture and subcultures (specifically, during the imaging period), the imaging device 10 takes still pictures of the objective cell groups placed in the dish at every predetermined timing (e.g., every 6 or 12 minutes) by the imaging function based on the control by the culture management device 31 or the operation by the manager, and generates the objective image data as the time-lapse images. The generated objective image data is recorded in the culture management device 31 together with the time information indicating the imaging time (the first and second phases in FIG. 11).

Also, the culture management device 31 executes the culture management processing (i.e., the determination processing) according to the second embodiment after the primary culture, each of the subcultures or the subcultures of a predetermined number of times. Then, the culture management device 31 calculates the mixing ratio of the objective cell to the objective cell groups in each dish, and executes the pass determination of the quality of the objective cell image of each dish based on the predetermined mixing ratio condition (i.e., the pass determination in the inspection processing) (the first and second phases in FIG. 11).

The mixing ratio condition may be changed at the time of the determination processing of each culture (the passing standard may be set higher for the initial cultures). The mixing condition may be kept unchanged at the time of the determination processing of each culture, or a mixing ratio condition different from other determination processing may be used only at the time of the determination processing of a certain culture.

Then, for the objective cell groups in the dish determined as Failed, the culture management device 31 executes processing (hereinafter referred to as "inhibition processing") for inhibiting culture of the unnecessary cells such as removing (or killing) the cell groups of unnecessary cell species, or executes the preparation processing for making the culture management device 31 to execute the inhibition processing (the first and second phases in FIG. 11).

Specifically, as the inhibition processing, the culture management device 31:

(1) identifies the unnecessary cell group (specifically, the fibroblast) and the necessary cell group (specifically, the skeletal myoblast) from an entire area of the image by a pattern matching (color or shape) or based on the migration speed, and (2) removes the cell group of the unnecessary cell species contactlessly by irradiating a near-infrared laser on the cell group of the unnecessary cell species.

For example, when the pattern matching is used in the processing (1), the culture management device 31 compares each cell with the data stored in advance and indicating the form of the fibroblast, and identifies the cells clearly different from the skeletal myoblast and similar to the fibroblast (e.g., the cell having a coincidence ratio equal to or larger than 90% with the data of the fibroblast).

Figure 12A:
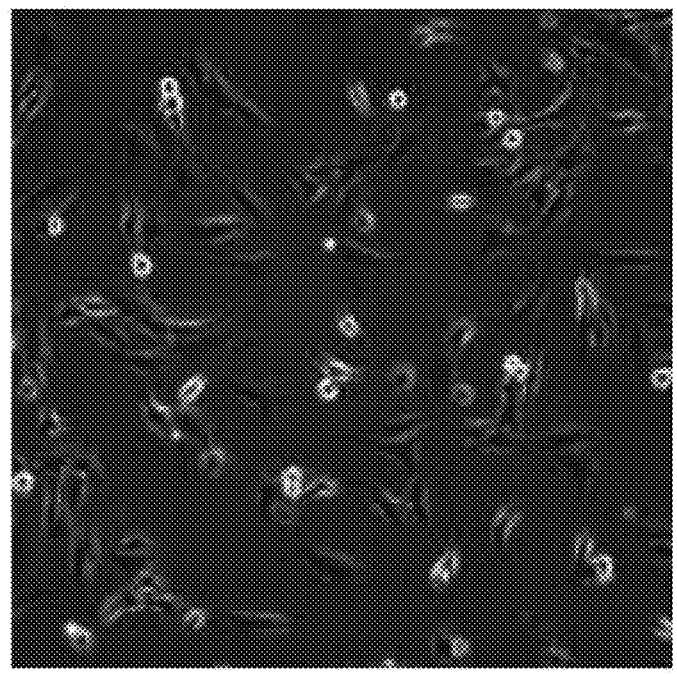
FIG. 12A is a diagram illustrating a phase contrast image of objective cell groups of a mouse imaged by a phase contrast microscope, used to explain identifying fibroblasts from the objective cell groups in which the fibroblasts and skeletal myoblasts are mixed.
Figure 12B:
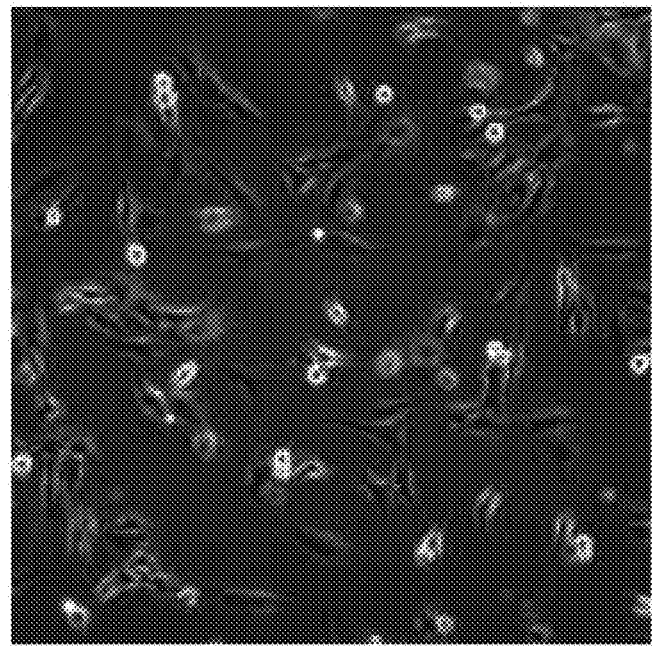
FIG. 12B is a diagram illustrating an image of the objective cell groups in which the fibroblasts in the objective cell groups are fluorescently dyed, used to explain identifying the fibroblasts from the objective cell groups in which the fibroblasts and the skeletal myoblasts are mixed.

For example, as shown in FIGS. 12A and 12B, in the objective cell groups during culture in which the skeletal myoblasts and the fibroblasts are mixed, it is shown that the form of the fibroblast is remarkably different from the skeletal myoblast, in theory. Therefore, it is normally possible to identify the fibroblast by the pattern matching.

The fibroblast sometimes has a form similar to the skeletal myoblast, or the skeletal myoblast sometimes has a form similar to the fibroblast. However, in the present invention, since the objective cell groups are determined to be usable when the mixing ratio is larger than a constant ratio, the cells hard to discriminate as described above are not identified as the fibroblast, and only the cells surely identified as the fibroblast are killed.

FIG. 12A is a phase contrast image of the objective cell groups of a mouse taken by the phase contrast microscope, and the image of the objective cell groups during coculture of C2C12 (mouse myoblast) and Swiss3T3 (mouse fibroblast) in which the skeletal myoblasts and the fibroblasts are mixed. FIG. 12B is a figure in which the fibroblasts are fluorescently dyed in FIG. 12A.

Then, the culture management device 31 irradiates a near-infrared laser on the cells identified as the fibroblast to be killed.

On the other hand, as the preparation processing, the culture management device 31 executes the notification to the manager urging the execution of the inhibition processing or the notification of the dish information therefor to the manager.

It is noted that Japanese patent application Laid-Open under No. 2016-154482 discloses a technique of identifying an area in which the objective cells are differentiated in the inhibition processing by an image analysis, and therefore its description will be omitted.

Next, when the primary culture and the subcultures of the objective cell groups end, the objective cell groups are cryopreserved until they are used (the third phase in FIG. 11), and the specification testing is executed when the objective cell groups are used (the fourth phase in FIG. 11).

Finally, the objective cell groups which have passed the specification testing are processed to the use form, e.g., processed to a sheet (the fifth phase in FIG. 11), and are used in regenerative medicine.

Particularly, the specification testing is a test for confirming whether or not the objective cell groups are suitable for the use in regenerative medicine, and is a test appropriately determined in accordance with the situation and/or contents of using the objective cell groups.

BRIEF DESCRIPTION OF REFERENCE NUMBERS

1 Cell quality evaluation system
2 Culture management system
10 Imaging device
20 Network
30 Image processing device
31 Culture management device
300 Data recording unit
301 Application recording unit
302 Image data recording unit
303 Reference data recording unit
310 Communication control unit
320, 400 Data processing unit
321 Detection processing unit
322 Generation processing unit
323 Estimation processing unit
324 Determination processing unit
340 Display unit
350 Display control unit
370 Operation unit
380 Management control unit
390 Output unit
391 Timer
410 Culture management unit
420 Notification control unit

The invention claimed is:

1. An image analysis system comprising:
an acquisition unit configured to acquire data of plural objective images, in which objective cell groups including plural kinds of cell groups having different attributes are imaged, in time series;
a detection unit configured to detect a migration speed of each cell imaged in the objective images by analyzing the acquired plural objective images;
a generation unit configured to generate a distribution function or a distribution state of the migration speeds of the imaged objective cell groups based on the detected migration speed of each cell; and
an estimation unit configured to estimate a mixing ratio of each of the plural kinds of cell groups based on migration speed information, recorded in a storage unit in advance and including information of the migration speed of each of the plural kinds of cell groups, and the generated distribution function or the generated distribution state.

2. The image analysis system according to claim 1, further comprising a determination unit configured to determine quality of the objective cell groups as passed when the estimated mixing ratio satisfies a predetermined condition.

3. The image analysis system according to claim 1,
wherein the migration speed information is information indicated by the distribution function, and
wherein the generation unit uses a normal distribution or a log normal distribution as the distribution function based on the detected migration speed of each cell.

4. The image analysis system according to claim 1,
wherein the migration speed information is information indicating the distribution state of the migration speeds,
wherein the generation unit calculates a histogram of the detected migration speed of each cell as the distribution state, and
wherein the estimation unit estimates the mixing ratio of each of the plural kinds of cell groups based on the migration speed information and a distribution shape of the histogram.

5. The image analysis system according to claim 1, further comprising an imaging device configured to image the objective cell groups placed in a container,
wherein the acquisition unit acquires the data of the objective images from the imaging device.

6. A non-transitory computer-readable medium storing a program causing a computer to function as:
- an acquisition unit configured to acquire data of plural objective images, in which objective cell groups including plural kinds of cell groups having different attributes are imaged, in time series;
- a detection unit configured to detect a migration speed of each cell imaged in the objective images by analyzing the acquired plural objective images;
- a generation unit configured to generate a distribution function or a distribution state of the migration speeds of the imaged objective cell groups based on the detected migration speed of each cell; and
- an estimation unit configured to estimate a mixing ratio of each of the plural kinds of cell groups based on migration speed information, recorded in a storage unit in advance and including information of the migration speed of each of the plural kinds of cell groups, and the generated distribution function or the generated distribution state.

7. An image analysis method comprising the steps of:
- acquiring data of plural objective images, in which objective cell groups including plural kinds of cell groups having different attributes are imaged, in time series;
- detecting a migration speed of each cell imaged in the objective images by analyzing the acquired plural objective images;
- generating a distribution function or a distribution state of the migration speeds of the imaged objective cell groups based on the detected migration speed of each cell; and
- estimating a mixing ratio of each of the plural kinds of cell groups based on migration speed information, recorded in a storage unit in advance and including information of the migration speed of each of the plural kinds of cell groups, and the generated distribution function or the generated distribution state.

8. A culture management system which manages a state of objective cell groups including plural kinds of cell groups having different attributes in a predetermined culture period, comprising:
- an acquisition unit configured to acquire data of plural objective images, in which objective cell groups including plural kinds of cell groups having different attributes are imaged, in time series at a predetermined timing in the culture period;
- a detection unit configured to detect a migration speed of each cell imaged in the objective images by analyzing the acquired plural objective images;
- a generation unit configured to generate a distribution function or a distribution state of the migration speeds of the imaged objective cell groups based on the detected migration speed of each cell;
- an estimation unit configured to estimate a mixing ratio of each of the plural kinds of cell groups based on migration speed information, recorded in a storage unit in advance and including information of the migration speed of each of the plural kinds of cell groups, and the generated distribution function or the generated distribution state;
- a determination unit configured to execute determination processing which determines whether or not the mixing ratio of each of the plural kinds of cell groups at the predetermined timing satisfies a predetermined mixing ratio condition; and
- a notification unit configured to execute a predetermined notification of a result of the determination processing to a manager.

9. The culture management system according to claim 8, wherein the estimation unit estimates the mixing ratio of each of the plural kinds of cell groups at every predetermined timing in the culture period, and
wherein the determination unit executes the determination processing at every predetermined timing while changing the mixing ratio condition.

10. The culture management system according to claim 9, in the determination processing at a timing of a short elapsed time in the culture period, the mixing ratio condition stricter than the mixing ratio condition used in the determination processing at a timing of a long elapsed time is used.

11. The culture management system according to claim 8, wherein the estimation unit estimates the mixing ratio of the objective cell groups including the plural kinds of cell groups classified by different doubling times.

12. A non-transitory computer-readable medium storing a program for managing a state of objective cell groups including plural kinds of cell groups having different attributes in a predetermined culture period, the program causing a computer to function as:
- an acquisition unit configured to acquire data of plural objective images, in which objective cell groups including plural kinds of cell groups having different attributes are imaged, in time series at a predetermined timing in the culture period;
- a detection unit configured to detect a migration speed of each cell imaged in the objective images by analyzing the acquired plural objective images;
- a generation unit configured to generate a distribution function or a distribution state of the migration speeds of the imaged objective cell groups based on the detected migration speed of each cell;
- an estimation unit configured to estimate a mixing ratio of each of the plural kinds of cell groups based on migration speed information, recorded in a storage unit in advance and including information of the migration speed of each of the plural kinds of cell groups, and the generated distribution function or the generated distribution state;
- a determination unit configured to execute determination processing which determines whether or not the mixing ratio of each of the plural kinds of cell groups at the predetermined timing satisfies a predetermined mixing ratio condition; and
- a notification unit configured to execute a predetermined notification of a result of the determination processing to a manager.

13. A culture management method for managing a state of objective cell groups including plural kinds of cell groups having different attributes in a predetermined culture period, comprising the steps of:
- acquiring data of plural objective images, in which objective cell groups including plural kinds of cell groups having different attributes are imaged, in time series at a predetermined timing in the culture period;
- detecting a migration speed of each cell imaged in the objective images by analyzing the acquired plural objective images;
- generating a distribution function or a distribution state of the migration speeds of the imaged objective cell groups based on the detected migration speed of each cell;

estimating a mixing ratio of each of the plural kinds of cell groups based on migration speed information, recorded in a storage unit in advance and including information of the migration speed of each of the plural kinds of cell groups, and the generated distribution function or the generated distribution state;

executing determination processing which determines whether or not the mixing ratio of each of the plural kinds of cell groups at the predetermined timing satisfies a predetermined mixing ratio condition; and executing a predetermined notification of a result of the determination processing to a manager.

14. A cell production method for producing at least a specific kind of cell group by controlling culture of objective cell groups collected from a living body and including plural kinds of cell groups having different attributes in a predetermined culture period, the method comprising the steps of:

executing inspection processing including determination processing which determines whether or not a mixing ratio of each of the plural kinds of cell groups included in the objective cell groups being cultured at a predetermined timing in the culture period satisfies a predetermined mixing ratio condition; and executing inhibition processing of inhibiting culture of unnecessary cell species in the objective cell groups when the mixing ratio of each of the plural kinds of cell groups does not satisfy the mixing ratio condition, or executing preparation processing for executing the inhibition processing, wherein the inspection processing comprising the steps of:

acquiring data of plural objective images, in which the objective cell groups including plural kinds of cell groups having different attributes are imaged, in time series at a predetermined timing;

detecting a migration speed of each cell imaged in the objective images by analyzing the acquired plural objective images;

generating a distribution function or a distribution state of the migration speeds of the imaged objective cell groups based on the detected migration speed of each cell; and estimating a mixing ratio of each of the plural kinds of cell groups based on migration speed information, recorded in a storage unit in advance and including information of the migration speed of each of the plural kinds of cell groups, and the generated distribution function or the generated distribution state, and executing the determination processing based on the mixing ratio condition.

15. The cell group production method according to claim 14, further comprising the step of:

estimating the mixing ratio of each of the plural kinds of cell groups at every predetermined timing in the culture period; and determining that the cultured objective cell groups are usable when the mixing ratio of each of the plural kinds of cell groups satisfies the mixing ratio condition in the determination processing executed at a time of an end of the culture period.

16. The cell group production method according to claim 15, further comprising the step of processing the objective cell groups into a use form when the cultured objective cell groups are determined to be usable.

17. The cell group production method according to claim 14, wherein, in the determination processing at a timing of a short elapsed time in the culture period, the mixing ratio condition stricter than the mixing ratio condition used in the determination processing at a timing of a long elapsed time is used.

* * * * *